United States Patent [19]

Calverley et al.

[11] Patent Number: 4,866,048

[45] Date of Patent: Sep. 12, 1989

[54] NOVEL VITAMIN D ANALOGUES

[75] Inventors: Martin J. Calverley, Ballerup; Ernst T. Binderup, Tåstrup, both of Denmark

[73] Assignee: Leo Pharmaceutical Products Ltd., Ballerup, Denmark

[21] Appl. No.: 34,391

[22] PCT Filed: Jul. 14, 1986

[86] PCT No.: PCT/DK86/00081

§ 371 Date: Mar. 18, 1987

§ 102(e) Date: Mar. 18, 1987

[87] PCT Pub. No.: WO87/00834

PCT Pub. Date: Feb. 12, 1987

[30] Foreign Application Priority Data

Aug. 2, 1985 [GB] United Kingdom ............... 8519502

[51] Int. Cl.$^4$ .......................... A61K 31/59; C07J 9/00
[52] U.S. Cl. .................................. 514/167; 260/397.2
[58] Field of Search ...................... 514/167; 260/397.2

[56] References Cited

U.S. PATENT DOCUMENTS

| | | | |
|---|---|---|---|
| 4,225,596 | 9/1980 | Deluca | 260/397.2 |
| 4,335,120 | 6/1982 | Holick et al. | 514/167 |
| 4,391,802 | 7/1983 | Suda et al. | 514/908 |
| 4,442,093 | 4/1984 | Maeda et al. | 514/167 |
| 4,610,978 | 9/1986 | Dikstein et al. | 514/167 |
| 4,661,294 | 4/1987 | Holick et al. | 260/397.2 |

OTHER PUBLICATIONS

Chemical Abstracts, vol. 102, No. 14; Apr. 8, 1985, #119659m, Dikstein et al.
Handbook of Nonprescription Drugs; 6th ed. (1979), pp. 397-400.

Primary Examiner—Douglas W. Robinson
Assistant Examiner—Joseph A. Lipovsky
Attorney, Agent, or Firm—Cushman, Darby & Cushman

[57] ABSTRACT

This invention relates to vitamin D analogues represented by the general formula I in which formula X stands for hydrogen, lower alkyl, halogen or hydroxy; Y stands for hydrogen or hydroxy; $R^1$ and $R^2$, which may be the same or different, stand for lower alkyl, optionally substituted with halogen or hydroxy with the proviso that $R^1$ and $R^2$ cannot both be methyl when X is other than lower alkyl, or, taken together with the carbon atom numbered 25, $R^1$ and $R^2$ can form a saturated or unsaturated $C_3$-$C_9$ carbocyclic ring which may optionally be substituted at any possible position(s) with lower alkyl, halogen or hydroxy; $R^3$ stands for hydrogen or lower alkyl; $R^4$ and $R^5$ represent either each hydrogen, or when taken together constitute a bond, with the result that a double bond connects carbon atoms numbered 22 and 23; and bioreversible derivatives thereof.

The compounds of the invention have a favorable therapeutic index and are particularly useful in the treatment of human and veterinary disorders which are characterized by abnormal cell proliferation and/or cell differentiation.

16 Claims, No Drawings

NOVEL VITAMIN D ANALOGUES

This invention relates to a hitherto unknown class of compounds which shows strong activity in inducing differentiation and inhibiting undesirable proliferation of certain cells, including cancer cells and skin cells, to pharmaceutical preparations containing these compounds, to dosage units of such preparations, and to their use in the treatment of diseases characterized by abnormal cell differentiation and/or cell proliferation.

The compounds of the invention constitute a novel class of vitamin D analogues and are represented by the general formula I

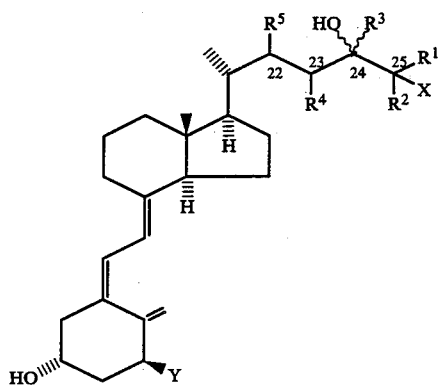

in which formula (and also throughout the remainder of this disclosure) X stands for hydrogen, lower alkyl, halogen or hydroxy; Y stands for hydrogen or hydroxy; $R^1$ and $R^2$, which may be the same or different, stand for lower alkyl, optionally substituted with halogen or hydroxy (but with the proviso that $R^1$ and $R^2$ cannot both be methyl when X is other than lower alkyl), or, taken together with the carbon atom numbered 25, $R^1$ and $R^2$ can form a saturated or unsaturated $C_3$-$C_9$ carbocyclic ring (including an aromatic ring) which may optionally by substituted at any possible positions(s) with lower alkyl, halogen or hydroxy; $R^3$ stands for hydrogen or lower alkyl; $R^4$ and $R^5$ represent either each hydrogen, or when taken together constitute a bond, with the result that a double bond connects carbon atoms numbered 22 and 23; and the two undulated bonds to carbon 24 indicate that both R and S forms at this centre are within the scope of the invention. In the context of this invention the expression "lower alkyl" indicates a straight or branched saturated or unsaturated carbon chain with a content of from 1 to 6 atoms.

As it can be seen, the compounds of formula I, depending on the meanings of $R^1$, $R^2$, $R^3$, $R^4$ and $R^5$, and/or X, contain one or more additional asymmetric carbon atoms and/or double bonds, and may thus form stereoisomeric forms. The invention covers all these compounds in pure form and also mixtures of them. It should be noted, however, that our investigations indicate a notable difference in activity between the stereoisomeric forms. In addition, derivatives of I in which one or more of the hydroxy groups are masked as groups which can be reconverted to hydroxy groups in vivo are also within the scope of the invention ("bioreversible derivatives or pro-drugs of I")

Especially preferred are compounds of formula I in which Y is hydroxy and $R^3$ stands for hydrogen or methyl, and in particular compounds in which $R^4$ and $R^5$ taken together represent a bond, especially in such a way that the resulting 22,23-double bond has the trans configuration.

The term "bioreversible derivatives or prodrugs of I" includes, but is not limited to, derivatives of the compounds of formula I in which one or more hydroxy groups have been transformed into —O—acyl or —O—glycosyl groups, such masked groups being hydrolyzable in vivo.

It has recently been shown that certain vitamin D derivatives, in particular $1,25(OH)_2D_3$ ($1\alpha,25$-dihydroxy-vitamin $D_3$) are able to stimulate the differentiation of cells and inhibit excessive cell proliferation, and it has been suggested that these compounds might be useful in the treatment of diseases characterized by abnormal cell proliferation and/or cell differentiation such as leukemia, myelofibrosis and psoriasis. However, the well known potent effects of these compounds on calcium metabolism prohibit the use of higher doses, which will give rise to hypercalcemia. Thus, these compounds are not completely satisfactory for use as drugs in the treatment of e.g. psoriasis or leukemia, which may require continuous administration of the drug in relatively high doses.

It has not surprisingly turned out that the compounds of the invention have a favourable therapeutic index and are particularly useful in the treatment of human and veterinary disorders which are characterized by abnormal cell proliferation and/or cell differentiation, such as certain dermatological disorders including psoriasis and certain cancer forms, e.g. leukemia and myelofibrosis.

A number of cells, including skin cells and cancer cells, contain receptors for $1,25(OH)_2D_3$. The compounds of the invention have thus been tested in vitro for their ability to interact with the receptor in such cells, and for their effect on the proliferation and differentiation of such cells (e.g. the human monocytic tumour cell line U 937). In vivo, the compounds were tested after p.o. and i.p. administration to rats for effects on calcium metabolism. The compounds were compared with $1,25(OH)_2D_3$ in the in vitro experiments and with $1\alpha(OH)D_3$ and $1,25(OH)_2D_3$ in the in vivo experiments.

From the above tests, it was shown that e.g. compound 59* binds strongly to the receptor and is a potent inhibitor of cell proliferation and inducer of cell differentiation in vitro. In vivo, compared to $1,25(OH)_2D_3$ and $1\alpha(OH)D_3$, it showed only weak vitamin D activity and could be administered at much higher doses without having any toxic effects.

\* See Table 2

Thus, a favourable separation of the biological effects on cell differentiation/proliferation and on calcium metabolism has been clearly demonstrated.

Compound I can be prepared by total synthesis, or, more conveniently, by partial synthesis from readily available precursors, either steroidal, for example dinorcholenic acid, ergosterol, stigmasterol, or seco-steroidal e.g. vitamin $D_2$. The route described below by way of example utilises vitamin $D_2$ as starting material, and is considered to be the most flexible of the routes explored to date, being very suitable for the synthesis of a large number of compounds represented by formula I. However, it should be noted that the synthesis of a particular compound on a production scale may well be more conveniently carried out from an alternative starting material and/or by an alternative route. Two such routes are outlined later on. The compound I can readily be obtained in crystalline form by crystallization from common organic solvents or mixtures thereof, as well known in the art.

The synthetic strategy involves the modification of the ring D side chain present in the (seco-)steroidal precursor to a 1S-formylethyl group followed by elaboration of the new side chain present in the particular target compound I. At some stage in the synthesis the rest of the full vitamin D skeleton must be elaborated. The way this is done in practice depends on the starting material and the new side chain in question, and in addition the order of some of the reaction steps can be altered with the result that not all the possible intermediates can be exemplified here. Furthermore, the nature of the various activating groups, protecting groups, and methods for masking the triene moiety can be different to those exemplified. However, any such changes still fall within the scope of this invention.

One synthetic route will now be described in detail. In the reaction scheme, the triene moiety of the vitamin D nucleus is masked as the adduct with $SO_2$ (other dienophiles which can be used include for example 4-phenyl-1,2,4-triazoline-3,5-dione and phthalazine-1,4-dione, as known in the art), and the ring A hydroxyl groups are protected as tert-butyl-dimethylsilyl (t-BuMe$_2$Si) ethers (other suitable protecting groups are well known in the art and include the etherifying and esterifying groups e.g. as described in "Protective Groups in Organic Synthesis", T. W. Greene, Wiley, New York, 1981). The coupling of the aldehyde function with a side chain fragment is done at the 5,6-trans vitamin stage (other possibilities include the cis-vitamin stage or masked triene stage, the requisite aldehyde being obtained by altering the order of reactions). The incorporation of the side chain fragment involves a Wittig reaction (other types of coupling, e.g. aldol reaction, or reaction with a sulphone anion, followed by elimination or reductive elimination, are well known in the art), the ylide being a triphenylphosphorane (other types of ylide being well known in the art). Finally, [X] represents either X of formula I, or a protected or masked derivative which can be converted to X at some stage in the synthesis (and not necessarily the last stage as indicated on the Scheme).

As shown on the Reaction Scheme which follows, the synthesis involves the preparation of the important key intermediate 12 which is used to prepare compounds of formula I in which Y stands for OH. The corresponding compound I in which Y=H is prepared analogously from 13. An alternative key intermediate is the corresponding 5,6-cis aldehyde 14, which can be used analogously to 13 or 12 in the subsequent step on the Scheme to give the corresponding 5,6-cis isomer of II and hence III. Reaction h then converts these isomers directly to the corresponding V. The continuation of the synthesis after 12 or 13 (or 14) requires the reaction with a side chain fragment (D), the synthesis of which can be achieved for example by the following route:-

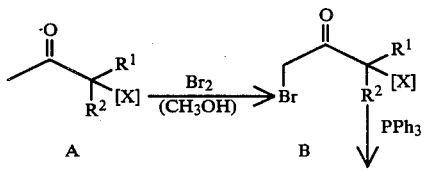

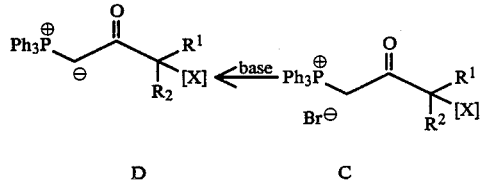

The side chain fragments shown in Table I are selected for the purposes of illustration and are described in the Preparations.

TABLE I

| Side Chain Fragment (D) | $R^1$ | $R^2$ | X or [X] |
|---|---|---|---|
| D(i) | —(CH$_2$)$_2$— | | H |
| D(ii) | —(CH$_2$)$_4$— | | H |
| D(iii) | —(CH$_2$)$_5$— | | H |
| D(iv) | CH$_3$ | CH$_3$ | CH$_3$ |
| D(v) | =CH—(CH=CH)$_2$— | | |

The ketone A, if not commercially available, may be prepared by literature methods and is converted to the bromomethyl ketone B by literature methods. In some cases B are commercially available starting materials.

In the Preparations, the starting materials/intermediates A, B and C (if desired) are also given corresponding suffixes (i)-(v) to indicate the nature of $R^1$, $R^2$ and [X] (e.g. for the sequence A(i)→B(i)→C(i)→D(i)). In order to describe further the invention, but not in any way to limit it, the details for the synthesis of some particular examples of compounds of formula I are given.

For the purpose, the Reaction Scheme and Notes should be read with reference to Tables 1 and 2 and to the Preparations and Examples.

NOTES TO REACTION SCHEME

On the Scheme, Z' represents an optionally protected hydroxy group, and Z also represents an optionally protected hydroxy group (which may be the same or different to Z') unless it is stated that Z=H, in which case Z represents hydrogen. For the specific numbered compounds described in Table 2 and in the Preparations and Examples, Z'=t-BuMe$_2$SiO, and Z=Z' unless stated otherwise, which requires step "b" to be a tert-butyldimethylsilylation reaction e.g. with t-BuMe$_2$CiCl-imidazzole) and step "j" to be a de-tert-butyldimethylsilylation reaction (e.g. with n-Bu$_4$NF). a. $SO_2$; b. Optional hydroxyl protection reaction; c. NaHCO$_3$ (boiling EtOH); d. SeO$_2$-N-methylmorpholine N-oxide (MeOH—CH$_2$Cl$_2$); e. (i) O$_3$ (ii) PPh$_3$; f. Side chain fragment D (see Table 1); g. 1,4-Reduction under suitable conditions with a selective reducing agent, e.g. Na$_2$S$_2$O$_4$ under phase transfer conditions; h. Formal source of "$R^3 \ominus$"-when $R^3$=H; e.g. NaBH$_4$ or other reducing agent; when $R^3$=alkyl, e.g. Grignard or other organometallic reagent. A radiolabel can be conveniently introduced at this stage by using a suitable source of radioactive $R^3$ (e.g. for $R^3 = {}^3H$ or ${}^{14}CH_3$); i. hγ-triplet sensitizer; j. Optional hydroxyl deprotection reaction(s); k. Any necessary reaction (sequence) for converting [X] to X.

Reaction Scheme
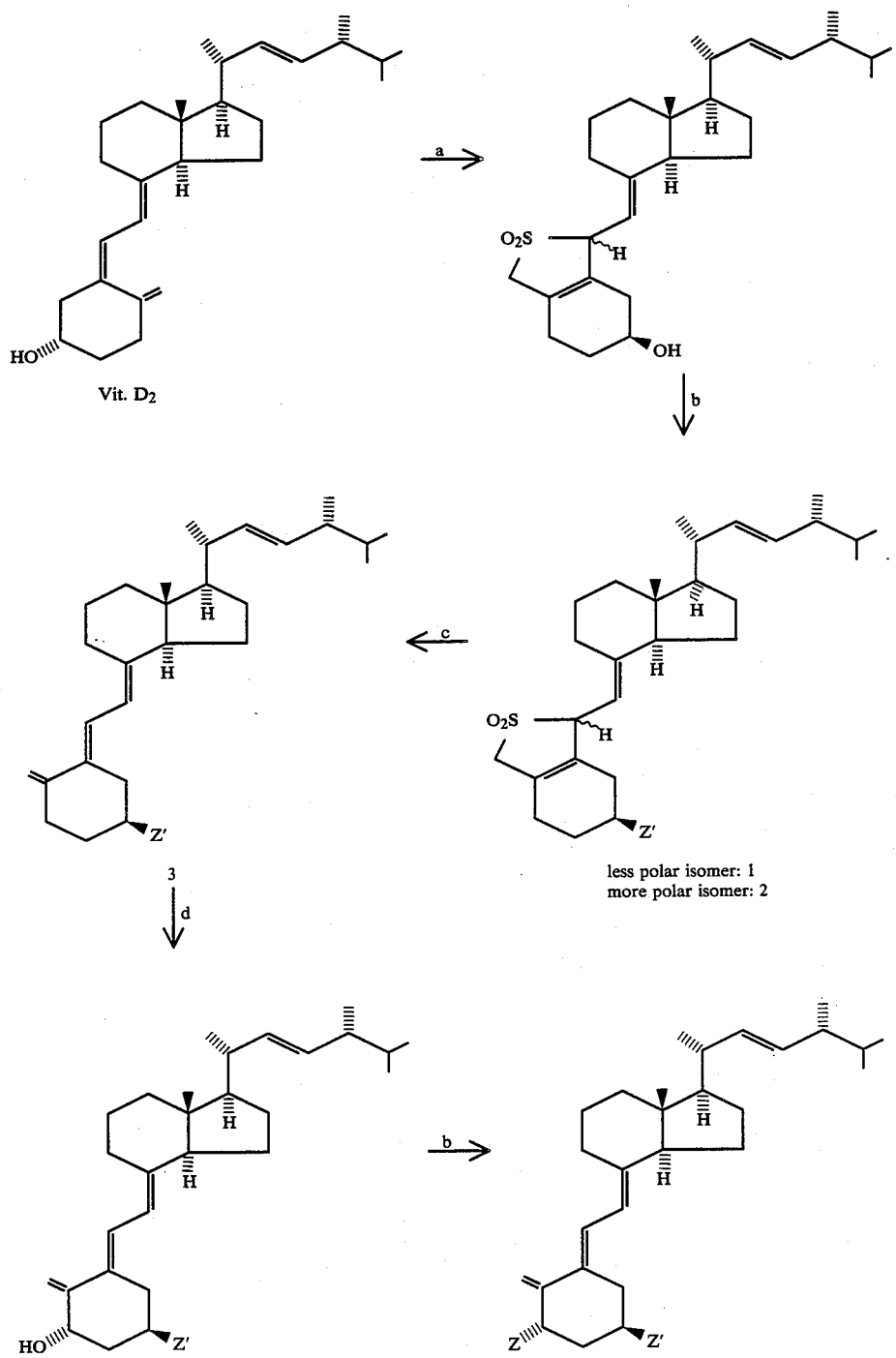

-continued
Reaction Scheme
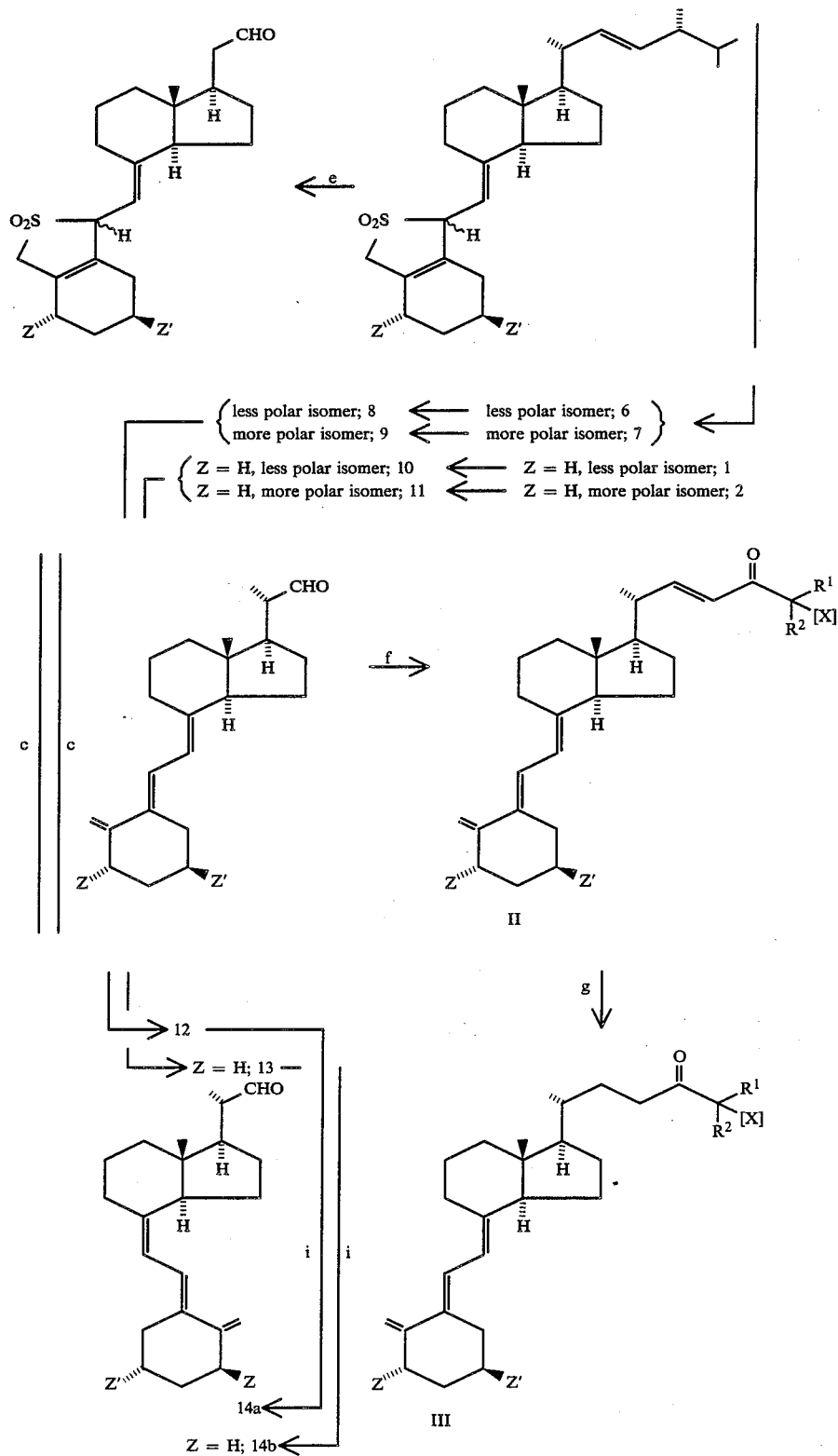

-continued
Reaction Scheme
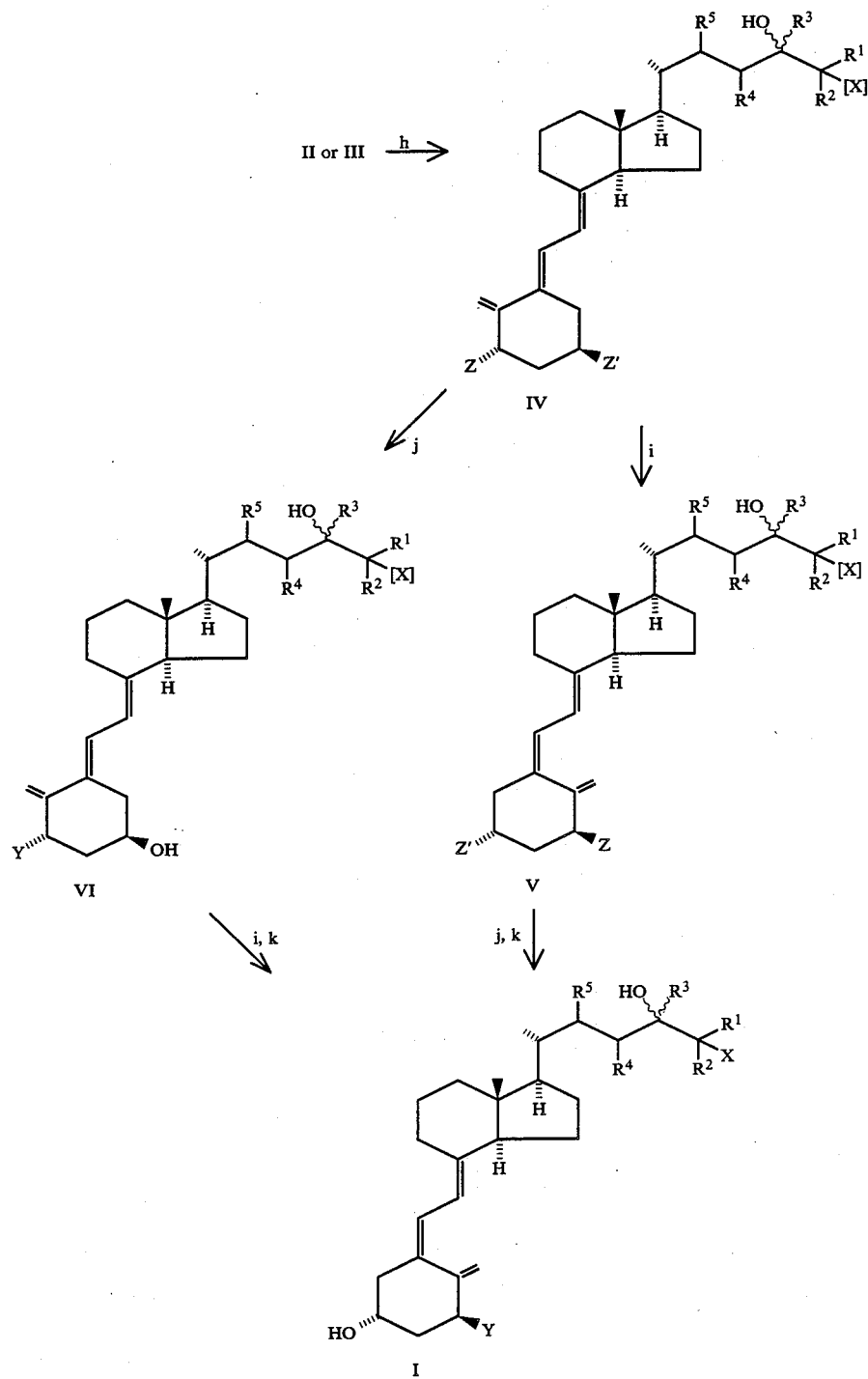
TABLE 2
Compounds Indicated on the Reaction Scheme and/or
Referred to by Number in the Preparations and Examples
| Compound Number | Formula (Z' = t-BuMe$_2$SiO) | | | | | | | |
|---|---|---|---|---|---|---|---|---|
| | | Y or Z | X or [X] | R$^1$ | R$^2$ | R$^3$ | R$^4$ | R$^5$ |
| 15 | II | H | H | —(CH$_2$)$_2$— | | — | — | — |
| 16 | II | t-BuMe$_2$SiO | H | —(CH$_2$)$_2$— | | — | — | — |

TABLE 2-continued

Compounds Indicated on the Reaction Scheme and/or
Referred to by Number in the Preparations and Examples

| Compound Number | Y or Z | X or [X] | R¹ | R² | R³ | R⁴ | R⁵ |
|---|---|---|---|---|---|---|---|
| 17 | II | t-BuMe₂SiO | H | —(CH₂)₄— | — | — | |
| 18 | II | t-BuMe₂SiO | H | —(CH₂)₅— | — | — | |
| 19 | II | t-BuMe₂SiO | CH₃ | CH₃ CH₃ | — | — | |
| 20 | II | t-BuMe₂SiO | —(CH=CH)₂—CH= | | — | — | |
| 21 | III | t-BuMe₂SiO | H | —(CH₂)₂— | — | — | |
| 22, 23 | IV | H | H | —(CH₂)₂— | H | bond | |
| 24, 25 | IV | t-BuMe₂SiO | H | —(CH₂)₂— | H | H | H |
| 26, 27 | IV | t-BuMe₂SiO | H | —(CH₂— | H | bond | |
| 28, 29 | IV | t-BuMe₂SiO | H | —(CH₂)₄— | H | bond | |
| 30, 31 | IV | t-BuMe₂SiO | H | —(CH₂)₄— | H | bond | |
| 32, 33 | IV | t-BuMe₂SiO | CH₃ | CH₃ CH₃ | H | bond | |
| 34, 35 | IV | t-BuMe-₂SiO | —(CH=CH)₂—CH= | | H | bond | |
| 36, 37 | IV | t-BuMe₂SiO | H | —(CH₂)₂— | CH₃ | bond | |
| 38, 39 | V | t-BuMe₂SiO | H | —(CH₂)₂— | H | bond | |
| 40, 41 | V | H | H | —(CH₂)₂— | H | bond | |
| 42, 43 | V | t-BuMe₂SiO | H | —(CH₂)₄— | H | bond | |
| 44, 45 | V | t-BuMe₂SiO | H | —(CH₂)₅— | H | bond | |
| 46, 47 | V | t-BuMe₂SiO | CH₃ | CH₃ CH₃ | H | bond | |
| 48, 49 | V | t-BuMe₂SiO | —(CH=CH)₂—CH= | | H | bond | |
| 50, 51 | V | t-BuMe₂SiO | H | —(CH₂)₂— | H | H | H |
| 52, 53 | V | t-BuMe₂SiO | H | —(CH₂)₂— | CH₃ | bond | |
| 54, 55 | VI | OH | H | —(CH₂)₂— | H | bond | |
| 72, 73 | VIII | OH | H | —(CH₂)₂— | H | bond | |
| 56, 57 | I | H | H | —(CH₂)₂— | H | bond | |
| 58, 59 | I | OH | H | —(CH₂)₂— | H | bond | |
| 60, 61 | I | OH | H | —(CH₂)₄— | H | bond | |
| 62, 63 | I | OH | H | —(CH₂)₅— | H | bond | |
| 64, 65 | I | OH | CH₃ | CH₃ CH₃ | H | bond | |
| 66, 67 | I | OH | —(CH=CH)₂—CH= | | H | bond | |

TABLE 2-continued

Compounds Indicated on the Reaction Scheme and/or Referred to by Number in the Preparations and Examples

| Compound Number | | Formula (Z' = t-BuMe$_2$SiO) | | | | | |
|---|---|---|---|---|---|---|---|
| | | Y or Z | X or [X] | R$^1$ | R$^2$ | R$^3$ | R$^4$ R$^5$ |
| 68 69 | I | OH | H | —(CH$_2$)$_2$— | | H | H H |
| 70 71 | I | OH | H | —(CH$_2$)$_2$— | | CH$_3$ | bond |

Notes.
(a) Where "bond" appears in the last column, the trans configuration of the 22,23-double bond is to be understood;
(b) Each formula I, IV, V, VI and VIII (and IX and XI, see later), represents two deparate numbered compounds. These differ only in their absolute configuration at C-24. In the Preparations and Examples, no attempt has been made to identify these configurations, but it is clearly indicated which of the two isomers is concerned in relative terms by differentiating unambiguously between their physical and/or spectroscopic properties (when possible) and/or by correlation with a particular starting material.

The compounds I may also be synthesized from steroidal precursors. Such an approach is illustrated in the conversion of the compound VII(a) or VII(b) (both available from dinorcholenic acid acetate) into the "pre-vitamin" VIII(a) or VIII(b), respectively, as outlined below:-

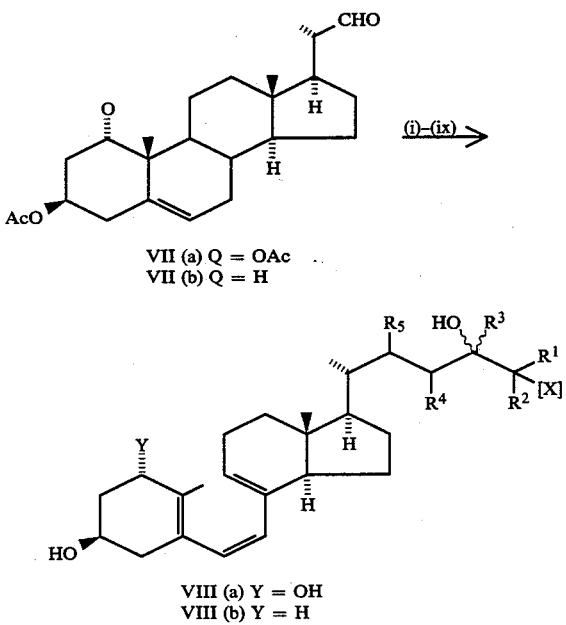

VII (a) Q = OAc
VII (b) Q = H

VIII (a) Y = OH
VIII (b) Y = H (i) Side Chain Fragment (D) (see text) (dimethyl sulphoxide, 100° C.);
(ii) N-bromosuccinimide (CCl$_4$, reflux);
(iii)(a) Bu$_4$NBr, then (b) Bu$_4$NF (tetrahydrofuran (THF), 20° C.);
(iv) 4-Phenyl-1,2,4-triazoline-3,5-dione (CHCl$_3$, 20° C.);
(v)* Na$_2$S$_2$O$_4$/(C$_{10}$H$_{21}$)$_3$NMeCl/NaHCO$_3$ PhH-H$_2$) reflux); either
(vi)+ NaBH$_4$/CeCl$_3$ (THF-MeOH, 0° C.) (for R$^3$=H); or
(vii)+ R$^3$MgBr or R$^3$Li (THF, −10° C.) (for R$^3$=C$_n$H$_{2n+1}$; n=1−6);
(viii) LiAlH$_4$ (THF, reflux);
(ix) Irradiation with medium-pressure Hg lamp through a Vycor filter (PhH-EtOH, 0° C.)

* If step (v) is included, the compounds VIII having R$^5$=R$^4$=H are produced; if step (v) is omitted, the compound VIII having R$^5$, R$^4$=bond (trans) are produced.
+ Chromatographic separation of C-24 epimers may be conveniently effected after stage (vi) or (vii).

The pre-vitamin VIII may be partially converted to the corresponding compound I by keeping in an inert solvent (e.g. ether, ethanol or benzene, or a mixture) at a temperature from about 0° C. to 100° C., preferably from about 20° C. to about 80° C. until equilibrium is reached or until an acceptable, less complete, conversion has been achieved (e.g. from two weeks at 20° C. to a few minutes at 80° C.). This equilibration may also be performed on a hydroxy-protected derivative of VIII, such as an acylated or trialkylsilylated derivative to give the corresponding derivative of I which is converted to I by conventional deprotection reaction(s).

Implicit in the routes to the compound I illustrated heretobefore is the key reaction establishing the 24-hydroxy group from a 24-oxo compound. The reactions exemplified all give rise to a mixture of diastereoisomers at this centre, which means that a separation step is required unless the particular compound I can be administered as a mixture. However, biological results have shown that of a pair of C-24 diastereoisomeric compounds I, one isomer is normally more active than the other. It is therefore advantageous to increase the proportion of the intermediate having the C-24 configuration corresponding to the more active compound I. This is possible by using a diastereoselective organometallic reagent (for R$^3$=alkyl) or reducing agent (for R$^3$=H). Methodology for the latter, reductive, reaction especially is now highly developed, and is particularly well applicable to compounds in which the 22,23-double bond is present in the 24-oxo intermediate.

Thus, the proportion of for example either compound IV (see Reaction Scheme) in the mixture, obtained by reducing compound II or III, can be increased by the use of for example the one or the other antipode of a chiral reducing agent. Examples of this type or reaction are reviewed for example in "Asymmetric Synthesis", ed. J. D. Morrison, Academic Press, London, Volume 2, 1983.

An alternative practical approach to an efficient reduction process is to recycle the undesired C-24 isomer (either in essentially pure form or admixed with smaller amounts of the desired isomer) after separation of either essentially all or just some of the desired isomer. This recycling is achieved by a mild oxidation back to the 24-oxo compound. For example, either compound 26 or 27 (or a mixture) is readily reconverted to 16 by reaction with active manganese dioxide.

It should be noted however that a minor amount of the less active C-24 isomer of I in admixture with the more active isomer does not interfere with the efficacy of the formulated drug.

A second alternative synthesis of compound I is illustrated in the coupling of an optionally hydroxy-protected form of the "top-half" fragment IX of the molecule with the anion derived from the protected "botton-half" fragment X to give XI, followed by conventional deprotection step(s) and any necessary modification of [X].

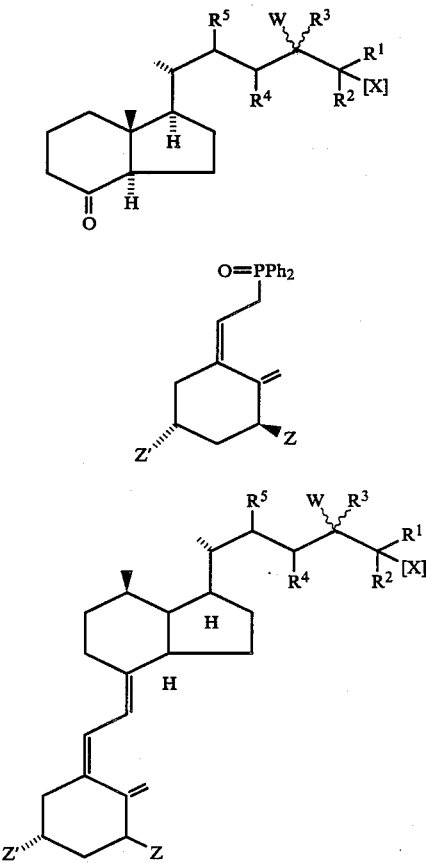

In formulae IX, X and XI, Z' is protected OH, e.g. t-BuSiMe$_2$O; Z is either H or protected OH, e.g. t-BuSiMe$_2$O; W is either OH or protected OH, e.g. t-BuSiMe$_2$O; and [X] is either X of formula I or a group which can be converted to X.

The present compounds are intended for use in pharmaceutical compositions which are useful in the treatment of human and veterinary disorders which, as mentioned above, are characterized by abnormal cell-proliferation and/or differentiation.

The amount required of a compound of formula I (hereinafter referred to as the active ingredient) for therapeutic effect will, of course, vary both with the particular compound, the route of administration and the mammal under treatment. The compounds of the invention can be administered by the parenteral, enteral or topical routes. They are well absorbed when given enterally and this is the preferred form of administration in the treatment of systemic disorders. In the treatment of dermatological disorders like psoriasis, topical forms like ointments, creams or lotions are preferred. In the treatment of systemic disorders daily doses of from 1–1000 μg, preferably from 2–250 μg, of a compound of formula I are administered. In the topical treatment of dermatological disorders, ointments, creams or lotions containing from 1–1000 μg/g, and preferably from 10–500 μg/g, of a compound of formula I are administered. The oral compositions are formulated, preferably as tablets, capsules, or drops, containing from 0.5–500 μg, preferably from 1–250 μg, of a compound of formula I, per dosage unit.

While it is possible for an active ingredient to be administered alone as the raw chemical, it is preferable to present it as a pharmaceutical formulation. Conveniently, the active ingredient comprises from 1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefor and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active or dispersing agent. Moulded tablets may be made by moulding, in a suitable machine,a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applications; oil-in-water or water-in-oil emulsions such as creams, ointments or pastes; or solutions or suspensions such as drops.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

The compositions may further contain other therapeutically active compounds usually applied in the treatment of the above mentioned pathological conditions.

The invention will now be further described in the following non-limiting Preparations and Examples.

PREPARATIONS AND EXAMPLES

General

The compounds referred to in the Preparations and Examples are to be identified by number (Compounds 15-73 via Table 2) with the corresponding formulae in the Reaction Scheme or elsewhere in which $Z'=$ t-BuMe$_2$SiO, and $Z=Z'$ unless otherwise stated.

For the cognate Preparations and Examples, only differences in the procedure and the new data are noted.

Analytical thin layer chromatography (TLC) was performed on Merck plates pre-coated with silica gel 60 F$_{254}$. The approximate Rf values quoted are only meant to be used for distinction in relative terms between pairs of isomers. Analytical high-performance liquid chromatography was performed on Lichrosorb Si 60 normal phase column (4 mm i.d.×25 cm) at a flow rate of 3.5 ml/min. with 2% methanol in dichloromethane as eluant. The quoted retention times, $T_R$, are used only for distinction in relative terms between pairs of isomers, and are not necessarily exactly reproducible. Nuclear magnetic resonance (NMR) ($\delta$) spectra were run at 100 MHz for solutions in CDCl$_3$ using either TMS ($\delta=0$) or CHCl$_3$ ($\delta=7.25$) as internal standard. Coupling constants are given in Hertz and are approximated to the nearest unit. Mass spectra (m/z) were run at 70 eV and only the highest mass signal and base peak are quoted. Organic solutions were dried over dried magnesium sulphate.

Preparation 1

Compound 5 (via Compounds 1 and/or 2, 3, and 4)

Vitamin D$_2$ (12.5 g) was dissolved in liquid SO$_2$ (50 ml) and the mixture stirred under reflux for 30 min. The SO$_2$ was distilled off, and the residue was dried in vacuo to give a foam. This was dissolved in N,N-dimethylformamide (100 ml), and imidazole (4.5 g) and tert-butyldimethylsilyl chloride (5 g) were added. The mixture was stirred under N$_2$ for 90 min. and then partitioned between ethyl acetate and water. The organic layer was washed with water, dried and concentrated to give a mixture of 1 and 2 as a crystalline solid which was triturated with ethanol, filtered off, and dried in vacuo.

[A portion of the mixture was separated by chromatography (silica; 30% ether in petroleum ether as eluant) to give pure 1, less polar isomer, needles (from dichloromethane-ethanol), $\delta$ 0.06 (6 H, s), 0.67 (3 H, s), 0.88 (9 H, s), 1.03 (3 H, d, J 7 Hz), 3.64 (2 H, broad s), 4.0 (1 H, m), 4.44–4.8 (2 H, 2 broad d, J 10 Hz) and 5.2 (2 H, m); m/z 510 M$^+$ $-$SO$_2$) and 119, and pure 2, more polar isomer, needles (from dichloromethane-ethanol); $\delta$ 0.06 (6 H, s), 0.58 (3 H, s), 0.88 (9 H, s), 1.03 (3 H, d, J 7 Hz), 3.65 (2 H, broad s), 3.95 (1 H, m), 4.5–4.9 (2 H, 2 broad d, J 10 Hz), and 5.2 (2 H, m); m/z 510 (M$^+$ $-$SO$_2$) and 119.]

The product (the pure isomers can also be used separately) was suspended in 96% ethanol (250 ml) and sodium hydrogen carbonate (20 g) added. The stirred mixture was heated under reflux for 100 min under N$_2$, cooled, partially concentrated in vacuo, and partitioned between ethyl acetate and water. The organic layer was washed with water, dried and concentrated to give 3, $\delta$ 0.07 (6 H, s), 0.57 (3 H, s), 0.88 (9 H, s), 1.02 (3 H, d, J 6 Hz), 3.85 (1 H, m), 4.64 (1 H, broad s), 4.91 (1 H, broad s), 5.2 (2 H, m), 5.85 (1 H, d, J 11 Hz), and 6.47 (1 H, d, J 11 Hz).

This was dissolved in dichloromethane (160 ml) containing dried N-methyl morpholine N-oxide (15 g). The stirred solution was heated under reflux under N$_2$ and a solution of selenium dioxide (3 g) in methanol (160 ml) was added rapidly. Heating under reflux was continued for 50 min. before the reaction mixture was cooled, diluted with more dichloromethane, washed with water, dried and concentrated to give 4, of sufficient purity for use in the next stage. [An analytical sample was obtained after chromatography (silica gel; 15% ether in petroleum ether as eluant), $\lambda_{max}$ (EtOH) 270 nm; $\delta$ 0.07 (6 H, s), 0.57 (3 H, s), 0.87 (9 H, s), 1.02 (3 H, d, J 7 Hz), 4.2 (1 H, m), 4.5 (1 H, m), 4.94 (1 H, broad s), 5.06 (1 H, broad s), 5.2 (2 H, m), 5.86 (1 H, d, J 11 Hz), and 6.51 (1 H, d, J 11 Hz).]

This was dissolved in N,N-dimethylformamide (80 ml), and imidazole (3.8 g) and tert-butyldimethylsilyl chloride (4.5 g) was added. The mixture was stirred under N$_2$ for 90 min. and then partitioned between ethyl acetate and water. The ethyl acetate layer was washed with water, dried and concentrated to give a crystalline solid which was purified by chormatography on silica (eluting with 2% ether in petroleum ether) followed by recrystallisation from ether-ethanol to give 5 as colourless needles), $\lambda_{max}$ (EtOH) 270 nm; $\delta$ 0.07 (12 H, s), 0.57 (3 H, s), 0.88 (9 H, s), 0.91 (9 H, s), 1.03 (3 H, d, J 7), 4.22 (1 H, broad s), 4.54 (1 H, broad dd, J 5 and 9 Hz), 4.97 (2 H, m), 5.20 (2 H, m), 5.82 (1 H, d, J 11 Hz), and 6.47 (1 H, d, J 11 Hz); m/z 640 (M$^+$) and 248.

Preparation 2

Compounds 6 and 7

5 (4.0 g) was dissolved in diethyl ether (10 ml) and liquid SO$_2$ (50 ml) and the mixture was stirred under reflux for 30 min. The SO$_2$ and ether were distilled off, and the residue was dried in vacuo to give white needles, showing two spits on thin layer chromatography (silica; 10% ether in petroleum ether as eluant) corresponding to 6 (Rf ca. 0.25) and 7 (Rf ca. 0.1). (Found: C, 67.97; H, 10.26; S, 4.37. C$_{40}$H$_{72}$O$_4$S Si$_2$ requires C, 68.12; H, 10.29; S, 4.55%); $\nu_{max}$ (CHCl$_3$) 1310 and 1160 cm$^{-1}$; $\delta$ 0.05 (12 H, broad s), 0.57 and 0.65 (3 H, 2 s), 0.87 (9 H, s), 0.88 (9 H, s), 3.4–4.1 (2 H, broad ABq, J 16 Hz), 4.17 (1 H, m), 4.35 (1 H, m) 4.7 (2 H, m) and 5.2 (2 H, m). Pure 6 and 7 were separated from a sample of the mixture by chromatography (silica; 20% ether in petroleum ether as eluant): 6, δ 0.65 (3 H, s) and 4.67 (2 H, m); 7, δ 0.57 (3 H, s) and 4.5–4.9 (2 H, 2 br d, J 10).

Preparation 3

Compounds 8 and 9

The mixture of 6 and 7 from Preparation 2 (4.4 g) was dissolved in dichloromethane (120 ml) and methanol (40 ml). The stirred solution was cooled in −60° C. and treated with ozonised oxygen until TLC showed essentially complete consumption of starting materials. The solution was then purged with $N_2$ and triphenyl phosphine (2.5 g) was added. After warming slowly to room temperature, the reaction mixture was diluted with more dichloromethane, washed with water, dried and concentrated. The residue was purified by chromatography (silica gel; 30% ether in petroleum ether as eluant). 8 and 9 can be collected separately or, more conveniently, as a mixture, which crystallises and was used directly in Preparation 6. The data refer to the separated isomers. First eluted was 8, obtained as white needles; $\nu_{max}$ (CHCl$_3$) 1720 (aldehyde), 1310 and 1160 cm$^{-1}$; δ 0.06 (12 H, broad s), 0.70 (3 H, s), 0.87 and 0.88 (18 H, 2 s), 1.13 (3 H, d, J 7 Hz), 3.45–4.1 (2 H, broad AB q, J 16 Hz), 4.2 (1 H, m), 4.35 (1 H, m), 4.7 (2 H, m), and 9.58 (1 H, d, J 3 Hz). Second eluted was 9, $\nu_{max}$ (CHCl$_3$) 1720 (aldehyde), 1310 and 1160 cm$^{-1}$; δ 0.07 (12 H, broad s), 0.61 (3 H, s), 0.88 and 0.89 (18 H, 2 H), 1.14 (3 H, d, J 7 Hz), 3.45–4.1 (2 H, broad AB q, J 16 Hz), 4.15 (1 H, m), 4.4 (1 H, m), 4.5–4.95 (2 H, 2 broad d, J 10 Hz), and 9.57 (1 H, d, J 3 Hz). It should be noted that the use of the pure isomers 6 and 7 separately as starting materials in this Preparation gives respectively 8 and 9 free from the other isomer.

Preparation 4

Compound 10

The use of compound 1 (from Preparation 1) (3.6 g) as starting material instead of 6 and/or 7 in Preparation 3, but using 50% ether in petroleum ether as eluant for the chromatography step, gave 10, δ 0.04 (6 H, br s), 0.70 (3 H, s), 0.86 (9 H, s), 1.13 (3 H, d, J 7), 3.63 (2 H, br s), 4.0 (1 H, m), 4.4–4.85 (2 H, 2 br, d, J 10) and 9.58 (1 H, d, J 3).

Preparation 5

Compound 11

The use of compound 2 (from Preparation 1) (3.5 g) as starting material instead of 6 and/or 7 in Preparation 3, but using 50% ether in petroleum ether as eluant for the chromatography step, gave 11, δ 0.04 (6 H, br s), 0.60 (3 H, s), 0.87 (9 H, s), 1.14 (3 H, d, J 7), 3.65 (2 H, br s), 4.0 (1 H, m), 4.5–4.95 (2 H, 2 br d, J 10) and 9.56 (1 H, d, J 3).

Preparation 6

Compound 12

The mixture of 8 and 9 from Preparation 3 (the pure isomers may also be used separately, but there is no advantage in separating them since both give 12 ethanol (50 ml) and sodium hydrogen carbonate (2 g) added. The stirred mixture was heated under reflux under $N_2$ for 100 min., cooled, partially concentrated in vacuo, and partitioned between ethyl acetate and water. The organic layer was washed with water, dried, and concentrated to give 12 of sufficient purity for subsequent use. An analytical sample was obtained after chromatography (silica gel; 5% ether in petroleum ether as eluant) and crystallization from ethanol; needles, m.p. 113°–5° C.; $\lambda_{max}$ (EtOH) 270 nm; $\nu_{max}$ (CHCl$_3$) 1720$^{-1}$ (aldehyde); δ 0.08 (12 H, s), 0.61 (3 H, s), 0.88 and 0.92 (18 H, 2 s) 1.16 (3 H, d, J 7 Hz), 4.2 (1 H, m), 4.5 (1 H, m), 4.98 (2 H, m), 5.85 (1 H, d, J 11 Hz), 6.46 (1 H, d, J 11 Hz), and 9.60 (1 H, d, J 3 Hz), m/z 572 (M+) and 248.

Preparation 7

Compound 13

The use of compound 10 or 11 (or a mixture) (0.9 g) as starting material instead of 8 and/or 9 in Preparation 6 gave 13, δ 0.06 (6 H, s), 0.61 (3 H, s), 0.88 (9 H, s), 1.14 (3 H, d, J 7), 3.85 (1 H, m), 4.65 (1 H, br s), 4.91 (1 H, br s), 5.88 (1 H, d, J 11), 6.48 (1 H, d, J 11), and 9.59 (1 h , d, J 13).

Preparation 8

Bromoacetylcyclopropane (B(i))

To a stirred, ice-cooled solution of acetylcyclopropane (A(i)) (22 g) in methanol (150 ml) was added bromine (40 g) at such a rate that the temperature was maintained below 20° C. Stirring was then continued at room temperature for 30 min. before water (75 ml) was added. After a further 15 min. the mixture was diluted with water (225 ml) and extracted with ether. The ether extracts were washed with saturated sodium carbonate solution, water, and dried. After removing the solvent in vacuo, the residue was distilled to give B(i), b.p. 71°–73° C./13 mmHg, δ 0.9–1.3 (4 H, m), 2.05–2.35 (1 H, m) and 4.02 (2 H, s).

Preparation 9

Cyclopropylcarbonylmethyltriphenylphosphonium bromide (C(i))

Starting material (B(i)), and triphenylphosphine were mixed in equimolar amounts and allowed to react spontaneously. The resulting solid cake was dissolved in dichloromethane and treated with ether to precipitate pure C(i) as colourless needles, m.p. 204°–205° C., δ 1.02 (4 H, m), 2.75 (1 H, m), 5.89 (2 H, d, J 12 Hz), and 7.45–8.0 (15 H, m).

Preparation 10

Cyclopentylcarbonylmethyltriphenylphosphonium bromide (C(ii))

Method: as Preparation 9; starting material: bromoacetylcyclopentane (B(ii)).

Preparation 11

Cyclohexylcarbonylmethyltriphenylphosphonium bromide (C(iii))

Method: as Preparation 9; Starting material: Bromoacetylcyclohexane (B(iii)); Data: m.p. 244°–7° C.

Preparation 12

Pivaloylmethyltriphenylphosphonium bromide (C(iv))

Method: as Preparation 9; Starting material: Bromomethyl tert-butyl ketone (B(iv)); Data: m.p. 234°–7° C.

Preparation 13

Phenacylmethyltriphenylphosphonium bromide (C(v))

Method: as Preparation 9; Starting material: phenacyl bromide (B(v)); Modification: B(v) and triphenylphosphine were predissolved and combined in toluene solution with stirring. After the spontaneous reaction, C(v) was filtered off and washed with ether; Data: m.p. >260° C.

Preparation 14

Cyclopropylcarbonylmethylemetriphenylphosphorane (D(i))

Starting material (C(i)) (3 g) was dissolved in dichloromethane (30 ml), and the solution was extracted with sodium hydroxide solution (2 N, 20 ml). The organic layer was washed with water, dried and concentrated in vacuo to give a product which was purified by recrystallisation from dichloromethane-acetone to give D(i) as needles, m.p. 181°–182° C. δ 0.60 (2 H, m), 0.85 (2 H, m), 1.75 (1 H, m), 3.77 (1 H, br d, J 26) and 7.1–7.8 (15 H, m).

Preparation 15

Cyclopentylcarbonylmethylenetriphenylphosphorane (D(ii))

Method: as Preparation 14; Starting material: C(ii); Data: m.p. 159°–60° C., δ 1.3–2.0 (8 H, m), 2.75 (1 H, m), 3.7 (1 H, d, J 27) and 7.2–7.8 (15 H, m).

Preparation 16

Cyclohexylcarbonylmethylenetriphenylphosphorane (D(iii))

Method: as Preparation 14; Starting material: C(iii); Data: m.p. 159°–61° C., δ 1.0–2.45 (11 H, m), 3.65 (1 H, m), and 7.2–7.9 (15 H, m).

Preparation 17

Pivaloylmethylenetriphenylphosphorane (D(iv))

Method: as Preparation 14; Starting material: C(iv); Data: m.p. 182°–3° C., δ 1.20 (9 H, s), 3.78 (1 H, d, J 27) and 7.2–7.8 (15 H, m).

Preparation 18

Phenacylmethylenetriphenylphosphorane (D(v))

Method: as Preparation 14; Starting material: C(v); Modification: recrystallisation from dichloromethane-ether; Data: m.p. 183°–4° C., δ 4.41 (1 H, d, J 25) and 7.2–8.0 (20 H, m).

Preparation 19

Compound 16

A solution stirred under $N_2$ of the aldehyde 12 (0.93 g) and the phosphorane D(i) (1 g) in dimethyl dulphoxide (20 ml) was heated at 95° C. for 90 min. then 105° C. for 120 min. after cooling, the reaction solution was partitioned between ethyl acetate and water. The ethyl acetate layer was washed with water, dried, and concentrated in vacuo to give a residue which was purified by chromatography (silica gel; 10% ether in petroleum ether as eluant) to give 16, colourless plates (from ether-methanol), m.p. 122°–123° C.; $\lambda_{max}$ (EtOH) 270 nm, δ 0.06 (12 H, s), 0.59 (3 H, s), 0.87 and 0.90 (18 H, 2 s), 1.13 (3 H, d, J 7), 4.2 (1 H, m), 4.5 (1 H, m), 4.96 (2 H, m), 5.8 (1 H, d, J 11 Hz), 6.14 (1 H, d, J 16 Hz), 6.45 (1 H, d, J 11 Hz), and 6.78 (1 H, dd, J 9 and 16 Hz); m/z 638 (M+) and 248.

Preparation 20

Compound 15

Method: as Preparation 19; Aldehyde: 13 (1.06 g); Phosphorane: D(i) (1.64 g); Data: δ 0.06 (6 H, s), 0.60 (3 H, s), 0.88 (9 H, s), 1.13 (3 H, d, J 7), 3.85 (1 H, m), 4.65 (1 H, br s), 4.92 (1 H, br s), 5.85 (1 H, d, J 11), 6.14 (1 H, d, J 16), 6.47 (1 H, d, J 11) and 6.78 (1 H, dd, J 9 and 16).

Preparation 21

Compound 17

Method: as Preparation 19; Aldehyde: 12 (1.62 g); Phosphorane: D(ii) (2.60 g); Reaction conditions: 16 h at 110° C.; Chromatography eluant: 5% ethyl acetate in petroleum ether; Data: δ 0.06 (12 H, s), 0.58 (3 H, s), 0.87 and 0.90 (each 9 H, s), 1.1 (3 H, d, J 7), 4.2 (1 H, m), 4.5 (1 H, m), 4.96 (2 H, m), 5.81 (1 H, d, J 11) 6.44 (1 H, d, J 11) and 6.79 (1 H, dd, J 9 and 15).

Preparation 22

Compound 18

Method: as Preparation 19; Aldehyde: 12 (1.0 g); Phosphorane: D(iii) (1.3 g); Reaction conditions: 4 h at 100° C. followed by 2 h at 110° C.; Chromatography eluant: 5% ethyl acetate in petroleum ether; Data: δ 0.06 (12 H, s), 0.58 (3 H, s), 0.87 and 0.90 (each 9 H, s), 1.1 (3 H, d, J 7), 4.2 (1 H, m), 4.5 (1 H, m), 4.96 (2 H, m), 5.81 (1 H, d, J 11), 6.44 (1 H, d, J 11) and 6.79 (1 H, dd, J 9 and 15).

Preparation 23

Compound 19

Method: as Preparation 19; Aldehyde: 12 (1.1 g); Phosphorane: D(iv) (2.1 g); Reaction conditions: 16 h at 110° C.; Chromatography eluant: 5% ether in petroleum ether; Data: δ 0.06 (12 H, s), 0.58 (3 H, s), 0.87 and 0.90 (each 9 H, s), 1.10 (3 H, d, J 7), 1.15 (9 H, s), 4.2 (1 H, m), 4.52 (1 H, m), 4.96 (2 H, m), 5.81 (1 H, d, J 11), 6.40 (1 H, d, J 15), 6.44 (1 H, d, J 11), and 6.80 (1 H, dd, J 9 and 15).

Preparation 24

Compound 20

Method: as Preparation 19; Aldehyde: 12 (0.96 g); Phosphorane: D(v) (1.86 g); Reaction conditions: 16 h at 110° C.; Chromatography eluant: 5% ether in petroleum ether; Data: δ 0.07 (12 H, s), 0.56 (3 H, s), 0.87 and 0.90 (each 9 H, s), 1.17 (3 H, d, J 7), 4.2 (1 H, m), 4.55 (1 H, m), 4.97 (2 H, m), 5.82 (1 H, d, J 11), 6.45 (1 H, d, J 11), 6.87 (2 H, m), 7.5 (3 H, m) and 7.9 (2 H, m).

Preparation 25

Compound 21

A mixture of 16 (200 mg), sodium hydrogen carbonate (0.5 g), sodium dithionite ($Na_2S_2O$) (0.5 g), and methyltridecylammonium chloride (0.05 g) in toluene (10 ml) and water (10 ml) under nitrogen was stirred vigorously at 80° C. for 1 h and then 85° C. for 30 min. After cooling, the reaction mixture was partitioned between ether and water, and the organic layer was washed with water, dried and concentrated in vacuo. The residue was purified by chromatography on silica gel (eluant: 10% ether in petroleum ether) to give 21, colorless plates (from ether-methanol); m.p. 93°–94° C., $\nu_{max}$ 1700 cm$^{-1}$; δ 0.06 (12 H, s), 0.55 (3 H, s), 0.87 and 0.90 (each 9 H, s), 4.2 (1 H, m), 4.5 (1 H, m), 4.96 (2 H, m), 5.82 (1 H, d, J 11) and 6.45 (1 H, d, J 11); m/z 640 (M+) and 248.

Preparation 26

Compounds 24 and 25

An ice-cooled, stirred solution of 21 (225 mg) in tetrahydrofuran (3 ml) was diluted with methanol (8 ml) and treated with sodium borohydride (140 mg) portionwise over 5 min. After further 10 minutes, the reaction mixture was partitioned between ethyl acetate and water, and the organic layer was washed with water, dried, and concentrated in vacuo. The residue was crystallized from ether-methanol to give 24 and 25 as needles. 24 and 25 have essentially superimposable NMR-spectra: δ 0.06 (12 H, s), 0.15–0.65 (4 H, m), 0.55 (3 H, s), 0.86 and 0.90 (each 9 H, s), 4.2 (1 H, m), 4.55 (1 H, m), 4.96 (2 H, m), 5.81 (1 H, d, J 11.5) and 6.46 (1 H, d, J 11.5).

Preparation 27

Compounds 26 and 27

To an ice-cooled, stirred solution of starting material 16 (100 mg) in tetrahydrofuran (10 ml) under nitrogen was added sodium bis(2-methoxyethoxy)aluminium hydride (70% solution in toluene) dropwise until TLC showed essentially complete consumption of starting material. The reaction mixture was then partitioned between ethyl acetate and sodium hydroxide solution (1 N), and the organic layer was washed with water, dried, and concentrated. The residue was purified by chromatography (silica gel; 10% ethyl acetate in petroleum ether as eluant) to give the title compounds. First eluted isomer was 26, δ 0.06 (12 H, s), 0.15–0.65 (4 H, m), 0.57 (3 H, s), 0.87 and 0.90 (18 H, 2 s), 1.05 (3 H, d, J 7 Hz), 3.45 (1 H, m), 4.2 (1 H, m), 4.55 (1 H, m), 4.96 (2 H, m), 5.51 (2 H, m), 5.82 (1 H, d, J 11 Hz) and 6.47 (1 H, d, J 11 Hz). This was followed by the more polar isomer 27, δ 0.06 (12 H, s), 0.15–0.65 (4 H, m), 0.57 (3 H, s), 0.87 and 0.90 (18 H, 2 s), 1.05 (3 H, d, J 7 Hz), 3.45 (1 H, m), 4.2 (1 H, m), 4.55 (1 H, m), 4.96 (2 H, m), 5.47 (2 H, m), 5.82 (1 H, d, J 11 Hz) and 6.47 (1 H, d, J 11 Hz). [It is notable that a characteristic difference in the position and pattern of the two proton multiplet δ ca. 5.5 in the NMR spectra is observed for each of the pairs of 24-epimers 26/27, 38/39, 54/55 and 58/59.] 26 and 27 were each obtained as needles from petroleum ether-methanol, m.p. 117°–118° C. and 122°–123° C., respectively.

Preparation 28

Compounds 26 and 27 (alternative method)

An ice-cooled, stirred solution of starting material 16 (0.82 g) in tetrahydrofuran (1 ml) was diluted with 0.4 N CeCl$_3$·6H$_2$O in methanol (4 ml) and further with methanol (2 ml), and treated with sodium borohydride (0.15 g), portionwise over 5 min. After a further 10 min., the reaction mixture was partitioned between ethyl acetate and water and the organic layer was washed with water, dried, and concentrated in vacuo. The residue was purified as described in Preparation 27, to give separately crystalline 26 and 27.

Preparation 29

Compounds 22 and 23

Method: as Preparation 27; Starting material: 15; Data: 22 (less polar isomer), δ 0.07 (6 H, s), 0.57 (3 H, s), 0.15–0.65 (4 H, m), 0.88 (9 H, s), 1.05 (3 H, d, J 7), 3.45 (1 H, m), 3.85 (1 H, m), 4.64 (1 H, broad s), 49.1 (1 H, broad s), 5.50 (2 H, m), 5.85 (1 H, d, J 11) and 6.47 (1 H, d, J 11); 23 (more polar isomer), δ 0.07 (6 H, s), 0.57 (3 H, s), 0.15–0.65 (4 H, m), 0.88 (9 H, s), 1.05 (3 H, d, J 7), 3.45 (1 H, m), 3.85 (1 H, m), 4.64 (1 H, broad s), 4.91 (1 H, broad s), 5.46 (2 H, m), 5.85 (1 H, d, J 11) and 6.47 (1 H, d, J 11).

Preparation 30

Compounds 28 and 29

Method as Preparation 28; Starting material: 17 (0.65 g); Data: 28 (less polar isomer); needles (from ether-methanol); δ 0.06 (12 H, s), 0.56 (3 H, s), 0.87 and 0.90 (each 9 H, s), 1.04 (3 H, d, J 7), 3.81 (1 H, m), 4.2 (1 H, m), 4.55 (1 H, m), 4.96 (2 H, m), 5.46 (2 H, m), 5.82 (1 H, d, J 11) and 6.45 (1 H, d, J 11); 29 (more polar isomer); needles (from ether-methanol; δ 0.06 (12 H, s), 0.56 (3 H, s), 0.87 and 0.90 (each 9 H, s), 1.05 (3 H, d, J 7), 3.78 (1 H, m), 4.2 (1 H, m), 4.55 (1 H, m), 4.96 (2 H, m), 5.42 (2 H, m), 5.82 (1 H, d, J 11) and 6.45 (1 H, d, J 11).

Preparation 31

Compounds 30 and 31

Method: as Preparation 28; Starting material: 18 (0.6 g); Data: 30 (less polar isomer); Needles (from methanol), m.p. 107°–108° C.; δ 0.06 (12 H, s), 0.56 (3 H, s), 0.87 and 0.90 (each 9 H, s), 1.05 (3 H, d, J 7), 3.75 (1 H, m), 4.2 (1 H, m), 4.55 (1 H, m), 4.96 (2 H, m), 5.44 (2 H, m), 5.81 (1 H, d, J 11) and 6.45 (1 H, d, J 11); 31 (more polar isomer); needles (from methanol), m.p. 85°–86° C.; δ 0.06 (12 H, s), 0.56 (3 H, s), 0.87 and 0.90 (each 9 H, s), 1.05 (3 H, d, J 7), 3.73 (1 H, m), 4.2 (1 H, m), 4.55 (1 H, m), 4.96 (2 H, m), 5.41 (2 H, m), 5.81 (1 H, d, J 11), and 6.45 (1 H, d. J 11).

Preparation 32

Compounds 32 and 33

Method: as Preparation 28; Starting material: 19 (0.5 g); Data: 32 (less polar isomer); needles (from methanol); δ 0.06 (12 H, s), 0.57 (3 H, s), 0.87 (9 H, s), 0.90 (18 H, s), 1.05 (3 H, d, J 7), 3.7 (1 H, m), 4.2 (1 H, m), 4.55 (1 H, m), 4.96 (2 H, m), 5.48 (2 H, m), 5.82 (1 H, d, J 11) and 6.45 (1 H, d, J 11); 33 (more polar isomer); needles (from methanol; δ 0.06 (12 H, s), 0.57 (3 H, s), 0.87 (9 H, s), 0.90 (18 H, s), 1.05 (3 H, d, J 7), 3.65 (1 H, m), 4.2 (1 H, m), 4.55 (1 H, m), 4.96 (2 H, m), 5.45 (2 H, m), 5.82 (1 H, d, J 11) and 6.45 (1 H, d, J 11).

Preparation 33

Compounds 34 and 35

Method: as Preparation 28; Starting material: 20 (197 mg); Modification: only 2 ml of CeCl$_3$ solution used; Data: 34 (less polar isomer) δ 0.06 (12 H, s), 0.57 (3 H, s), 0.87 and 0.91 (each 9 H, s), 1.06 (3 H, d, J 7), 4.2 (1 H, m), 4.55 (1 H, m), 4.96 (2 H, m), 5.16 (1 H, m), 5.63 (2 H, m), 5.81 (1 H, d, J 11), 6.46 (1 H, d, J 11) and 7.34 (5 H, m); 35 (more polar isomer); δ 0.06 (12 H, s), 0.55 (3 H, s), 0.87 and 0.91 (each 9 H, s), 1.08 (3 H, d, J 7), 4.2 (1 H, m), 4.55 (1 H, m), 4.96 (2 H, m), 5.16 (1 H, m), 5.61

(2 H, m), 5.81 (1 H, d, J 11), 6.46 (1 H, d, J 11) and 7.34 (5 H, m).

Preparation 34

Compounds 36 and 37

A stirred solution of 16 (146 mg) in tetrahydrofuran (4 ml) under nitrogen was cooled to about −20° C. and treated dropwise with methyl-lithium (ca. 1 M solution in ether) until TLC showed essentially complete consumption of starting material. The reaction mixture was then partitioned between ether and water and the organic layer was washed with water, dried, and concentrated. The residue was crystallised from ether-methanol containing a trace of triethylamine to give 36 and 37 as needles. Compounds 36 and 37 have essentially superimposable NMR spectra: δ 0.06 (12 H, s), 0.15–0.65 (4 H, m), 0.56 (3 H, s), 0.87 and 0.90 (each 9 H, s), 1.03 (3 H, d, J 7), 1,27 (3 H, s), 4.2 (1 H, m), 4.55 (1 H, m), 4.96 (2 H, m), 5.31 (1 H, d, J 16), 5.54 (1 H, dd, J 7, 16), 5.81 (1 H, d, J 11) and 6.46 (1 H, d, J 11).

Preparation 35

Compound 16 (from recycling of 26 and 27)

A solution of either 26, 27, or a mixture of these two compounds (0.5 g) in dichloromethane (30 ml) was stirred under nitrogen at room temperature with active manganese dioxide (4.0 g) for 6 h. The reaction mixture was filtered, concentrated and the residue purified as in Preparation 19 to give crystalline 16.

Preparation 36

Compound 38

A solution of starting material 26 (21 mg), anthracene (4 mg) and triethylamine (1 drop) in toluene (5 ml) under N₂ in a Purex flask was irradiated with light from a high pressure ultra-violet lamp, type TQ 150Z2 (Hanau) at room temperature for 100 min. The solution was filtered, concentrated in vacuo and the residue purified by chromatography (silica gel; 15% ethyl acetate in petroleum ether as eluant) to give 38, δ 0.06 (12 H, s), 0.15–0.65 (4 H, m), 0.55 (3 H, s), 0.88 (18 H, s), 1.05 (3 H, d, J 7 Hz), 3.5 (1 H, m), 4.2 (1 H, m), 4.35 (1 H, m), 4.85 (1 H, m), 5.17 (1 H, m), 5.50 (2 H, m), 5.99 (1 H, d, J 12 Hz) and 6.24 (1 H, d, J 12 Hz). It should be noted that in the eluant system specified above, 38 is less polar than and distinguishable on TLC from 39.

Preparations 37–51

Compounds 39–53

Using the method of Preparation 36, the following starting materials IV (20–30 mg) were converted to the corresponding products V, which were each purified by chromatography using the eluant system specified (the entry in the 'Eluant' column indicates the percentage of the more polar component of either an ethyl acetate (EtOAc) or ether (Et₂O) in petroleum ether mixture):

| Preparation | V | IV | Eluant | Data (for V) |
|---|---|---|---|---|
| 37 | 39 | 27 | 15% EtOAc | δ 0.06 (12 H, s), 0.15–0.65 (4 H, m), 0.55 (3 H, s), 0.88 (18 H, s), 1.05 (3 H, d, J 7), 3.45 (1 H, m), 4.2 (1 H, m), 4.35 (1 H, m), 4.85 (1 H, m), 5.17 (1 H, m), 5.46 (2 H, m), 5.99 (1 H, d, J 12) and 6.24 (1 H, d, J 12). |
| 38 | 40 | 22 | 15% EtOAc | δ 0.06 (6 H, s), 0.15–0.65 (4 H, m), 0.56 (3 H, s), 0.89 (9 H, s), 1.05 (3 H, d, J 7), 3.5 (1 H, m), 3.85 (1 H, m), 4.8 (1 H, m), 5.0 (1 H, m), 5.50 (2 H, m) and 6.1 (2 H, ABq, J 11). |
| 39 | 41 | 23 | 15% EtOAc | δ 0.06 (6 H, s), 0.15–0.65 (4 H, m), 0.56 (3 H, s), 0.89 (9 H, s), 1.05 (3 H, d, J 7), 3.45 (1 H, m), 3.85 (1 H, m), 4.8 (1 H, m), 5.0 (1 H, m), 5.47 (2 H, m) and 6.1 (2 H, ABq, J 11). |
| 40 | 42 | 28 | 10% Et₂O | δ 0.06 (12 H, s), 0.55 (3 H, s), 0.88 (18 H, s), 1.04 (3 H, d, J 7), 3.81 (1 H, m), 4.2 (1 H, m), 4.35 (1 H, m), 4.85 (1 H, m), 5.45 (2 H, m), 5.99 (1 H, d, J 12) and 6.24 (1 H, d, J 12) |
| 41 | 43 | 29 | 10% Et₂O | δ 0.06 (12 H, s), 0.55 (3 H, s), 0.88 (18 H, s), 1.04 (3 H, d, J 7), 3.78 (1 H, m), 4.2 (1 H, m), 4.35 (1 H, m), 4.85 (1 H, m), 5.41 (2 H, m), 5.99 (1 H, d, J 12) and 6.24 (1 H, d, J 12). |
| 42 | 44 | 30 | 10% Et₂O | δ 0.06 (12 H, s), 0.55 (3 H, s), 0.88 (18 H, s), 1.04 (3 H, d, J 7), 3.75 (1 H, m), 4.2 (1 H, m), 4.35 (1 H, m), 4.86 (1 H, m), 5.16 (1 H, m), 5.43 (2 H, m), 5.99 (1 H, d, J 12) and 6.24 (1 H, d, J 12). |
| 43 | 45 | 31 | 10% Et₂O | δ 0.06 (12 H, s), 0.55 (3 H, s), 0.88 (18 H, s), 1.04 (3 H, d, J 7), 3.73 (1 H, m), 4.2 (1 H, m), 4.35 (1 H, m), 4.86 (1 H, m), 5.16 (1 H, m), 5.41 (2 H, m), 5.99 (1 H, d, J 12) and 6.24 (1 H, d, J 12). |
| 44 | 46 | 32 | 10% Et₂O | δ 0.06 (12 H, s), 0.55 (3 H, s), 0.88 (18 H, s), 0.90 (9 H, s), 1.04 (3 H, d, J 7), 3.67 (1 H, m), 4.2 (1 H, m), 4.35 (1 H, m), 4.86 (1 H, m), 5.16 (1 H, m), 5.47 (2 H, m), 5.99 (1 H, d, J 12) and 6.24 (1 H, d, J 12). |
| 45 | 47 | 33 | 10% Et₂O | δ 0.06 (12 H, s), 0.55 (3 H, s), 0.88 (18 H, s), 0.90 (9 H, s), 1.04 (3 H, d, J 7), 3.63 (1 H, m), 4.2 (1 H, m), 4.35 (1 H, m), 4.86 (1 H, m), 5.16 (1 H, m), 5.43 (2 H, m), 5.99 (1 H, d, J 12), and 6.24 (1 H, d, J 12). |
| 46 | 48 | 34 | 10% Et₂O | δ 0.08 (12 H, s), 0.56 (3 H, s), 0.90 (18 H, s), 4.2 (1 H, m), 4.4 (1 H, m), 4.87 (1 H, m), 5.17 (2 H, m), 5.61 (2 H, m), 6.02 (1 H, d, J 11), 6.26 (1 H, d, J 11) and 7.34 (5 H, m). |
| 47 | 49 | 35 | 10% Et₂O | δ 0.08 (12 H, s), 0.56 (3 H, s), 0.90 (18 H, s), 4.2 (1 H, m), 4.4 (1 H, m), 4.87 (1 H, m), 5.17 (2 H, m), 5.59 (2 H, m), 6.02 (1 H, d, J 11), 6.26 (1 H, d, J 11) and 7.34 (5 H, m). |
| 48 | 50 | 24 | 30% Et₂O | δ 0.06 (12 H, s), 0.15–0.65 (4 H, m), 0.54 (3 H, s), 0.88 (18 H, s), 4.18 (1 H, m), 4.37 (1 H, m), 4.86 (1 H, m), 5.17 (1 H, m), 6.00 (1 H, d, J 12) and 6.24 (1 H, d, J 12). |
| 49 | 51 | 25 | 30% Et₂O | δ 0.06 (12 H, s), 0.15–0.65 |

-continued

| Preparation | V | IV | Eluant | Data (for V) |
|---|---|---|---|---|
| | | | | (4 H, m), 0.54 (3 H, s), 0.88 (18 H, s), 4.18 (1 H, m), 4.37 (1 H, m), 4.86 (1 H, m), 5.17 (1 H, m), 6.00 (1 H, d, J 12) and 6.24 (1 H, d, J 12). |
| 50 | 52 | 36 | 20% Et$_2$O | δ 0.06 (12 H, s), 0.15–0.65 (4 H, m), 0.55 (3 H, s), 0.88 (18 H, s), 1.02 (3 H, d, J 7), 1.26 (3 H, s), 4.2 (1 H, m), 4.35 (1 H, m), 4.85 (1 H, m), 5.17 (1 H, m), 5.31 (1 H, d, J 16), 5.54 (1 H, dd, J 7, 16), 5.99 (1 H, d, J 12) and 6.24 (1 H, d, J 12). |
| 51 | 53 | 37 | 20% Et$_2$O | δ 0.06 (12 H, s), 0.15–0.65 (4 H, m), 0.55 (3 H, s), 0.88 (18 H, s), 1.02 (3 H, d, J 7), 1.26 (3 H, s), 4.2 (1 H, m), 4.35 (1 H, m), 4.85 (1 H, m), 5.17 (1 H, m), 5.31 (1 H, d, J 16), 5.54 (1 H, dd, J 7, 16), 5.99 (1 H, d, J 12) and 6.24 (1 H, d, J 12). |

Preparation 52

Compound 14a (Z=Z'=OSiMe$_2$Bu$^t$)

Method: as Preparation 36; Starting material: 12 (28 mg); Modification: the triethylamine was omitted; Chromatography eluant: 5% ether in petroleum ether; δ 0.06 (12 H, s), 0.59 (3 H, s), 0.88 (18 H, s), 1.14 (3 H, d, J 7), 4.2 (1 H, m), 4.4 (1 H, m), 4.86 (1 H, m), 5.17 (1 H, m), 5.99 (1 H, d, J 12), 6.24 (1 H, d, J 12) and 9.58 (1 H, d, J 3).

Preparation 53

Compound 14b (Z=H, Z'=OSiMe$_2$Bu$^t$)

Method: as Preparation 36; Starting material: 13 (24 mg); Modification: the triethylamine was omitted; Chromatography eluant: 5% ether in petroleum ether; δ 0.06 (6 H, s), 0.60 (3 H, s), 0.88 (9 H, s), 1.14 (3 H, d, J 7), 3.85 (1 H, m), 4.78 (1 H, m), 4.99 (1 H, m), 6.1 (2 H, ABq, J 11) and 9.59 (1 H, d, J 3).

Preparation 54

Compound 54

A solution of starting material 26 (30 mg) and tetrabutylammonium fluoride (60 mg) in tetrahydrofuran (5 ml) was heated at 60° C. under N$_2$ for 60 min. After cooling, the reaction solution was partitioned between ethyl acetate and 2% sodium hydrogen carbonate solution, and the organic layer was washed with water, dried and concentrated. The residue was purified by chromatography (silica gel, ethyl acetate as eluant) to give 54, λ$_{max}$(EtOH) 265 nm, δ 0.15–0.65 (4 H, m), 0.58 (3 H, s), 0.8–1.1 (1 H, m), 1.05 (3 H, d, J 7), 3.5 (1 H, m), 4.2 (1 H, m), 4.5 (1 H, m), 4.97 (1 H, m), 5.11 (1 H, m), 5.51 (2 H, m), 5.88 (1 H, d, J 11) and 6.57 (1 H, d, J 11).

Preparation 55

Compound 55

Method: as Preparation 54; Starting material: 27 (26 mg); λ$_{max}$(EtOH) 265 nm, δ 0.15–0.65 (4 H, m), 0.58 (3 H, s), 0.8–1.1 (1 H, m), 1.05 (3 H, d, J 7), 3.45 (1 H, m), 4.5 (1 H, m), 4.97 (1 H, m), 5.11 (1 H, m), 5.48 (2 H, m), 5.88 (1 H, d, J 11) and 6.57 (1 H, d, J 11).

Preparation 56

Equilibration of compounds 59 and 73

A solution of 59 (73 mg) in ethanol (20 ml) was heated under reflux under nitrogen for 40 min. After cooling, the solvent was removed in vacuo, and the residue purified by chromatography (silica gel, ethyl acetate as eluant) to return 59 followed by the more polar 73, δ 0.15–0.65 (4 H, m), 0.72 (3 H, s), 0.8–1.1 (1 H, m), 1.05 (3 H, d, J 7), 3.45 (1 H, m), 4.2 (2 H, m), 5.47 (3 H, m) and 5.83 (2 H, m).

EXAMPLE 1

(1'E,3R,5Z,7E,20R)-9,10-seco-20-(3'-cyclopropyl-3'-hydroxyprop-1'-enyl)-3-hydroxypregna-5,7,10(19)-triene, isomer A (Compound 56)

A solution of starting material 40 (37 mg) and tetrabutylammonium fluoride (90 mg) in tetrahydrofuran (4 ml) was heated under reflux under N$_2$ for 1 h. After cooling, the reaction solution was partitioned between ethyl acetate and 2% sodium hydrogen carbonate solution, and the organic layer was washed with water, dried and concentrated. The residue was purified by chromatography (silica gel; 50% ethyl acetate in petroleum ether as eluant) to give 56, λ$_{max}$(EtOH) 265 nm, δ 0.15–0.65 (4 H, m) 0.55 (3 H, s), 1.05 (3 H, d, J 7), 3.5 (1 H, m), 3.94 (1 H, m), 4.81 (1 H, m), 5.02 (1 H, m), 5.50 (2 H, m), 6.01 (1 H, d, J 11) and 6.24 (1 H, d, J 11).

EXAMPLE 2

(1'E,3R,5Z,7E,20R)-9,10-seco-20-(3'-cyclopropyl-3'-hydroxyprop-1'-enyl)-3-hydroxypregna-5,7,10(19)-triene, isomer B (compound 57)

Method: as Example 1; Starting material: 41 (40 mg); Data: λ$_{max}$(EtOH) 265 nm, δ 0.15–0.65 (4 H, m), 0.55 (3H, s), 1.05 (3 H, d, J 7), 3.45 (1 H, m), 3.94 (1 H, m), 4.81 (1 H, m), 5.02 (1 H, m), 5.47 (2 H, m), 6.01 (1 H, d, J 11) and 6.24 (1 H, d, J 11).

EXAMPLE 3

(1S,1'E,3R,5Z,7E,20R)-(9,10)-seco-20-(3'-cyclopropyl-3'-hydroxyprop-1'-enyl)-1,3-dihydroxypregna-5,7,10(19)-triene, isomer A (compound 58)

Method: as Example 1; Starting material: 38 (15 mg); Chromatography eluant: ethyl acetate; Data: T$_R$ 10.4 min, λ$_{max}$(EtOH) 265 nm, δ 0.15–0.65 (4 H, m), 0.56 (3 H, s), 0.75–1.1 (1 H, m), 1.05 (3 H, d, J 7 Hz), 3.47 (1 H, m), 4.2 (1 H, m), 4.4 (1 H, m), 4.99 (1 H,m), 5.31 (1 H, m), 5.50 (2 H, m), 5.99 (1 H, d, J 11 Hz), and 6.36 (1 H, d, J 11 Hz); m/z 412 (M$^+$) and 134.

EXAMPLE 4

Compound 58 (alternative method)

A solution of 54 (15 mg), anthracene (4 mg) and triethylamine (20 mg) in toluene (5 ml) under N$_2$ in a Pyrex flask was irradiated with light from a high pressure untraviolet lamp, type TQ 150Z2 (Hanau) at room temperature for 100 min. The solution was concentrated in vacuo and the residue purified by chromatography (silica gel; ethyl acetate as eluant) to give 58.

EXAMPLE 5

(1S,1'E,3R,5Z,7E,20R)-(9,10)-seco-20-(3'-cyclopropyl-3'-hydroxyprop-1'-enyl)-1,3-dihydroxypregna-5,7,10(19)-triene, isomer B (compound 59)

A solution of 39 (45 mg) and tetrabutylammonium fluoride (90 mg) in tetrahydrofuran (4 ml) was heated under reflux under $N_2$ for 60 min. After cooling, the reaction solution was partitioned between ethyl acetate and 2% sodium hydrogen carbonate solution, and the organic layer was washed with water, dried and concentrated. The residue was purified by chromatography (silica gel; ethyl acetate as eluant) followed by crystallisation from methyl formate to give 59 as needles; m.p. 166°–168° C., $T_R$ 9.2 min, $\lambda_{max}$ (EtOH) 265 nm, δ 0.15–0.65 (4 H, m), 0.56 (3 H, s), 0.75–1.1 (1 H, m), 1.05 (3 H, d, J 7 Hz), 3.45 (1 H, m), 4.2 (1 H, m), 4.4 (1 H, m), 4.99 (1 H, m), 5.31 (1 H, m), 5.47 (2 H, m), 5.99 (1 H, d, J 11 Hz), and 6.36 (1 H, d, J 11 Hz); m/z 412 (M+) and 134.

EXAMPLE 6

Compound 59 (alternative method)

A solution of 55 (15 mg), anthracene (4 mg) and triethylamine (20 mg) in toluene (5 ml) under $N_2$ in a Pyrex flask was irradiated with light from a high pressure ultraviolet lamp, type TQ 150Z2 (Hanau) at room temperature for 100 min. The solution was concentrated in vacuo and the residue purified by chromatography (silica gel; ethyl acetate as eluant) to give 59.

EXAMPLE 7

Compound 59 (alternative method)

A solution of 73 (125 mg) in ether (9 ml) was kept under nitrogen in the dark at about 20° C. for 10 days. The solvent was removed in vacuo and the residue purified by chromatography (silica gel; ethyl acetate as eluant) followed by chrystallisation from methyl formate to give 59.

EXAMPLE 8

(1S,1'E,3R,5Z,7E,20R)-(9,10)-seco-20-(3'-cyclopentyl-3'-hydroxyprop-1'-enyl)-1,3-dihydroxypregna-5,7,10(19)-triene, isomer A (compound 60)

Method: as Example 1; Starting material 42 (49 mg); Chromatography eluant: ethyl acetate; Data: $\lambda_{max}$ (EtOH) 265 nm; δ 0.56 (3 H, s), 1.03 ('H, d, J 7), 3.8 (1 H, m), 4,2 (1 H, m), 4,4 (1 H, m), 4.98 (1 H, m), 5.31 (1 H, m), 5.45 (2 H, m), 5.99 (1 H, d, J 12) and 6.36 (1 H, d, J 12); m/z 440 (M+) and 1.34; $T_R$ 8.2 min.

EXAMPLE 9

(1S,1'E,3R,5Z,7E,20R)-(9,10)-seco-20-(3'-cyclopentyl-3'-hydroxyprop-1'-enyl)-1,3-dihydroxypregna-5,7,10(19)-triene, isomer B (compound 61)

Method: as Example 1; Starting material 43 (31 mg); Chromatography eluant: ethyl acetate; Data: $\lambda_{max}$ (EtOH) 265 nm; δ 0.55 (3 H, s), 1.03 (3 H, d, J 7), 3.77 (1 H, m), 4.2 (1 H, m), 4.4 (1 H, m), 4.98 (1 H, m), 5.31 (1 H, m), 5.41 (2 H, m), 5.99 (1 H, d, J 12) and 6.36 (1 H, d, J 12); m/z 440 (M+) and 134; $T_R$ 6.6 min.

EXAMPLE 10

(1S,1'E,3R,5Z,7E,20R)-(9,10)-seco-20-(3'-cyclohexyl-3'-hydroxyprop-1'-enyl)-1,3-dihydroxypregna-5,7,10(19)-triene, isomer A (compound 62)

Method: as Example 1; Starting material: 44 (40 mg); Chromatography eluant: ethyl acetate; Data: $\lambda_{max}$ (EtOH) 265 nm; δ 0.56 (3 H, s), 1.04 (3 H, d, J 7), 3.75 (1 H, m), 4.2 (1 H, m), 4.4 (1 H, m), 4.98 (1 H, m), 5.31 (1 H, m), 5.43 (2 H, m), 5.99 (1 H, d, J 12), 6.36 (1 H, d, J 12); m/z 454 (M+) and 134; $T_R$ 7.2 min.

EXAMPLE 11

(1S,1'E,3R,5Z,7E,20R)-(9,10)-seco-20-(3'-cyclohexyl-3'-hydroxyprop-1'-enyl)-1,3-dihydroxypregna-5,7,10(19)-triene, isomer B (compound 63)

Method: as Example 1; Starting material: 45 (41 mg); Chromatography eluant: ethyl acetate; Data: $\lambda_{max}$ (EtOH) 265 nm; δ 0.56 (3 H, s), 1.04 (3 H, d, J 7), 3.73 (1 H, m), 4.2 (1 H, m), 4.4 (1 H, m), 4.98 (1 H, m), 5.31 (1 H, m), 5.40 (2 H, m), 5.99 (1 H, d, J 12), 6.36 (1 H, d, J 12); m/z 454 (M+) and 134; $T_R$ 5.8 min.

EXAMPLE 12

(1S,1'E,3R,5Z,7E,20R)-(9,10)-seco-20-(4',4'-dimethyl-3'-hydroxybut-1'-enyl)-1,3-dihydroxypregna-5,7,10(19)-triene, isomer A (compound 64)

Method: as Example 1; Starting material: 46 (29 mg); Chromatography eluant: ethyl acetate; Data: $T_R$ 8.2 min, $\lambda_{max}$ (EtOH) 265 nm, δ 0.56 (3 H, s), 0.89 (9 H, s), 1.04 (3 H, d, J 7), 3.67 (1 H, m), 4.2 (1 H, m), 4.41 (1 H, m), 4.99 (1 H, br s), 5.31 (1 H, m), 5.47 (2 H, m), 6.00 (1 H, d, J 11) and 6.37 (1 H, d, J 11).

EXAMPLE 13

(1S,1'E,3R,5Z,7E,20R)-(9,10)-seco-20-(4',4'-dimethyl-3'-hydroxybut-1'-enyl)-1,3-dihydroxypregna-5,7,10(19)-triene, isomer B (compound 65)

Method: as Example 1; Starting material: 47 (27 mg) Chromatography eluant: ethyl acetate; Data: $T_R$ 6.8 min, $\lambda_{max}$ (EtOH) 265 nm, δ 0.56 (3 H, s), 0.88 (9 H, s), 1.04 (3 H, d, J 7), 3.63 (1 H, m), 4.2 (1 H, m), 4.40 (1 H, m), 4.99 (1 H, br s), 5.31 (1 H, m), 5.43 (2 H, m), 6.00 (1 H, d, J 11) and 6.36 (1 H, d, J 11).

EXAMPLE 14

(1S,1'E,3R,5Z,7E,20R)-(9,10)-seco-20-3'-hydroxy-3-phenylprop-1'-enyl)-1,3-dihydroxypregna-5,7,10(19)-triene, isomer A (compound 66)

Method: as Example 1; Starting material: 48 (29 mg); Chromatography eluant: ethyl acetate; Data: $T_R$ 8.2 min, $\lambda_{max}$ (EtOH) 265 nm, δ 0.56 (3 H, s), 1.04 (3 H, d, J 77), 4.2 (1 H, m), 4.40 (1 H, m), 4.98 (1 H, m), 5.12 (1 H, m), 5.31 (1 H, m), 5.60 (2 H, m), 6.00 (1 H, d, J 11), 6.36 (1 H, d, J 11) and 7.33 (5 H, m).

EXAMPLE 15

(1S,1'E,3R,5Z,7E,20R)-(9,10)-seco-20-(3'-hydroxy-3-phenylprop-1'-enyl)-1,3-dihydroxypregna-5,7,10(19)-triene, isomer B (compound 67)

Method: as Example 1; Starting material: 49 (42 mg); Chromatography eluant: ethyl acetate; Data: $T_R$ 7.2 min., $\lambda_{max}$ (EtOH) 265 nm, δ 0.54 (3 H, s), 1.06 (3 H, d, J 7), 4.2 (1 H, m), 4.42 (1 H, m), 4.97 (1 H, m), 5.13 (1 H, m), 5.30 (1 H, m), 5.59 (2 H, m), 5.99 (1 H, d, J 11), 6.36 (1 H, d, J 11) and 7.33 (5 H, m).

EXAMPLE 16

(1S,3R,5Z,7E,20R)-(9,10)-seco-20-(3'-cyclopropyl-3'-hydroxypropyl)-1,3-dihydroxypregna-5,7,10(19)-triene, isomer A (compound 68)

Method: as Example 1; Starting material: 50 (40 mg); Chromatography eluant: ethyl acetate; Data: $\lambda_{max}$ (EtOH) 265 nm, δ 0.15–0.65 (4 H, m), 0.54 (3 H, s), 0.93 (3 H, d, J 7), 4.2 (1H, m), 4.4 (1 H, m), 4.99 (1 H, m), 5.31 (1 H, m), 5.99 (1 H, d, J 12) and 6.36 (1 H, d, J 12).

EXAMPLE 17

(1S,3R,5Z,7E,20R)-(9,10)-seco-20-(3'-cyclopropyl-3'-hydroxypropyl)-1,3-dihydroxypregna-5,7,10(19)-triene, isomer B (compound 69)

Method: as Example 1; Starting material: 51 (22 mg); Chromatography eluant: ethyl acetate; Data: $\lambda_{max}$ (EtOH) 265 nm, δ 0.15–0.65 (4 H, m), 0.54 (3 H, s), 0.93 (3 H, d, J 7), 4.2 (1 H, m), 4.4 (1 H, m), 4.99 (1 H, m), 5.31 (1 H, m), 5.99 (1 H, d, J 12) and 6.36 (1 H, d, J 12).

EXAMPLE 18

(1S,1'E,3R,5Z,7E,20R)-(9,10)-seco-20-(3'-cyclopropyl-3'-hydroxy-but-1'-enyl)-1,3-dihydroxypregna-5,7,10(19)-triene, isomer A (compound 70)

Method: as Example 1; Starting material: 52 (19 mg); Chromatography eluant: ethyl acetate; Data: $\lambda_{max}$ (EtOH) 265 nm, δ 0.15–0.65 (4 H, m), 0.55 (3 H, s), 1.02 (3 H, d, J 7), 1.26 (3 H, s), 4.2 (1 H, m), 4.4 (1 H, m), 5.31 (1 H, d, J 16), 5.31 (1 H, m), 5.54 (1 H, dd, J 7 and 16), 5.99 (1 H, d, J 12) and 6.36 (1 H, d, J 12).

EXAMPLE 19

(1S,1'E,3R,5Z,7E,20R)-(9,10)-seco-20-(3'-cyclopropyl-3'-hydroxy-but-1'-enyl)-1,3-dihydroxypregna-5,7,10(19)-triene, isomer B (compound 71)

Method: as Example 1; Starting material: 53 (17 mg); Chromatography eluant: ethyl acetate; Data: $\lambda_{max}$ (EtOH) 265 nm, δ 0.15–0.65 (4 H, m), 0.55 (3 H, s), 1.02 (3 H, d, J 7), 1.26 (3 H, s), 4.2 (1 H, m), 4.4 (1 H, m), 5.31 (1 H, m), 5.54 (1 H, dd, J 7 and 16), 5.99 (1 H, d, J 12) and 6.36 (1 H, d, J 12).

EXAMPLE 20

Dermatological Cream Containing 59

In 1 g almond oil was dissolved 1 mg 59. To this solution was added 40 g of mineral oil and 20 g of self-emulsifying beeswax. The mixture was heated to liquify. After the addition of 40 ml hot water, the mixture was mixed well. The resulting cream contains approximately 10 μg of 59 per gram of cream.

EXAMPLE 21

Capsules containing 59

59 was dissolved in a triglyceride of a medium chain fatty acid to a final concentration of 50 μg 59/ml oil. 10 Parts by weight of gelatin, 5 parts by weight glycerine, 0.08 parts by weight potassium sorbate, and 14 parts by weight distilled water were mixed together with heating and formed into soft gelatin capsules. These were then filled each with 100 μl of the 59 in oil solution, such that each capsule contained 5 μg 59.

What we claim is:

1. A compound of the formula I

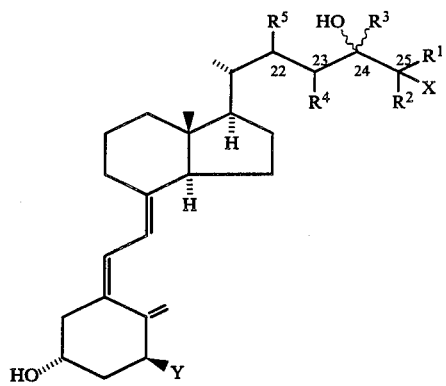

in which formula X stands for hydrogen, $C_1$–$C_6$-alkyl, halogen or hydroxy; Y stands for hydrogen or hydroxy; $R^1$ and $R^2$, taken together with the carbon atom numbered 25 form a saturated or unsaturated $C_3$–$C_9$ carbocyclic ring including an aromatic ring which may optionally be substituted at any possible position(s) with $C_1$–$C_6$-alkyl, halogen or hydroxy; $R^3$ stands for hydrogen or $C_1$–$C_6$-alkyl; $R^4$ and $R^5$ represent either each hydrogen, or when taken together constitute a bond with the result that a double bond connects carbon atoms numbered 22 and 23; and bioreversible derivatives thereof.

2. A compound according to claim 1, in crystalline form.

3. A compound according to claim 1, which is a compound of formula I in which $R^3$ is hydrogen or methyl.

4. A compound according to claim 3, in which $R^4$ and $R^5$ taken together represent a bond, the resulting 22,23 double bond having the trans configuration.

5. A compound according to claim 1, selected from the groups consisting of the 3'R and 3'S isomers of:
(1'E,3R,5Z,7E,20R)-9,10-seco-20-(3'-cyclopropyl-3'-hydroxyprop-1'-enyl)-3-hydroxypregna-5,7,10(19)-triene;
(1S,1'E,3R,5Z,7E,20R)-9,10-seco-20-(3'-cyclopropyl-3'-hydroxyprop-1'-enyl)-1,3-dihydroxypregna-5,7,10(19)-triene;
(1S,1'E,3R,5Z,7E,20R)-9,10-seco-20-(3'-cyclopentyl-3'-hydroxyprop-1'-enyl)-1,3-dihydroxypregna-5,7,10(19)-triene;
(1S,1'E,3R,5Z,7E,20R)-9,10-seco-20-(3'-cyclohexyl-3'-hydroxyprop-1'-enyl)-1,3-dihydroxypregna-5,7,10(19)-triene;
(1S,1'E,3R,5Z,7E,20R)-9,10-seco-20-(3'-phenyl-3'-hydroxyprop-1'-enyl)-1,3-dihydroxypregna-5,7,10(19)-triene;
(1S,3R,5Z,7E,20R)-9,10-(3'-cyclopropyl-3'-hydroxypropyl)-1,3-dihydroxypregna-5,7,10(19)-triene;
(1S,1'E,3R,5Z,7E,20R)-9,10-seco-20(3'-cyclopropyl-3'-hydroxybut-1'-enyl)-1,3-dihydroxypregna-5,7,10(19)-triene.

6. A method for producing a compound of claim 1, in which a compound of formula IV:

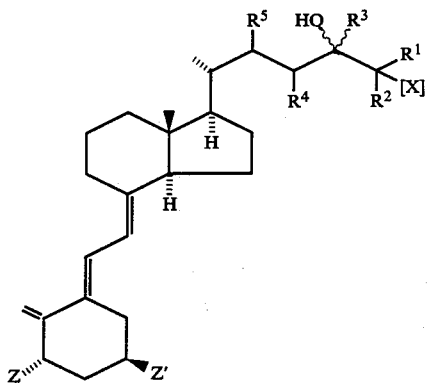

in which $R^1$, $R^2$, $R^3$, $R^4$ and $R^5$ are as defined above, [X] is X, as defined above, or a protected or masked derivative which can later be converted to X, Z' is an optionally protected hydroxy group, and Z is either H or an optionally protected hydroxy group, is subjected to a triplet-sensitized photoisomerisation and, if necessary, deprotected of the hydroxy group(s), the sequence of these reactions being arbitrary.

7. A method for producing a compound of formula IV of claim 6, in which compound N

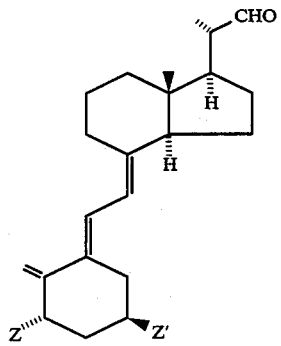

in which Z' and Z are as defined above, is reacted with a compound of formula D

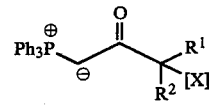

optionally followed by a reduction of the 22,23-double bond, and conversion of the 24-oxo compound into the 24-hydroxy compound of formula IV by treatment with a reducing agent ($R^3$=hydrogen) or an organometallic reagent ($R^3$=alkyl).

8. A compound of formula N of claim 7, which is (3R,5E,7E,20S)-9,10-seco-20-formyl-3-(tertbutyldimethylsilyloxy)pregna-5,7,10(19)-triene; or (1S,3R,5E,7E,20S)-9,10-seco-20-formyl-1,3-bis(tertbutyldimethylsilyloxy)pregna-5,7,10(19)-triene.

9. A method for producing a compound of formula I of claim 1, in which the corresponding pre-vitamin, optionally with one or more protected hydroxy groups, is subjected to thermal isomerization, if necessary followed by deprotection of the hydroxy group(s).

10. A compound according to claim 1 wherein $R^1$ and $R^2$ taken together with the carbon numbered 25, form a saturated carbocyclic ring.

11. A compound according to claim 1 wherein $R^1$ and $R^2$ taken together with the carbon numbered 25, form a saturated cyclopropyl ring.

12. A pharmaceutical preparation, containing an effective amount of one or more of the compounds of formula I of claim 1, together with pharmaceutically acceptable, non-toxic carriers and/or auxiliary agents.

13. A pharmaceutical preparation according to claim 12 in topical form.

14. A pharmaceutical preparation according to claim 12 in oral form.

15. A method for the treatment of patients suffering from disorders characterized by abnormal cell-proliferation and/or cell-differentiation, in which a preparation according to claim 12 is administered to the patient in need of treatment.

16. A method according to claim 15, in which patients suffering from psoriasis are treated with a preparation according to claim 13.

* * * * *

UNITED STATES PATENT AND TRADEMARK OFFICE
CERTIFICATE OF CORRECTION

PATENT NO. : 4,866,048             Page 1 of 5
DATED      : September 12, 1989
INVENTOR(S): Calverley et al It is certified that error appears in the above-identified patent and that said Letters Patent is hereby corrected as shown below:

Col. 4, line 52, "CiCl-imidazzole" should be --SiCl--imidazole--.

Col. 7, last formula should read:
--

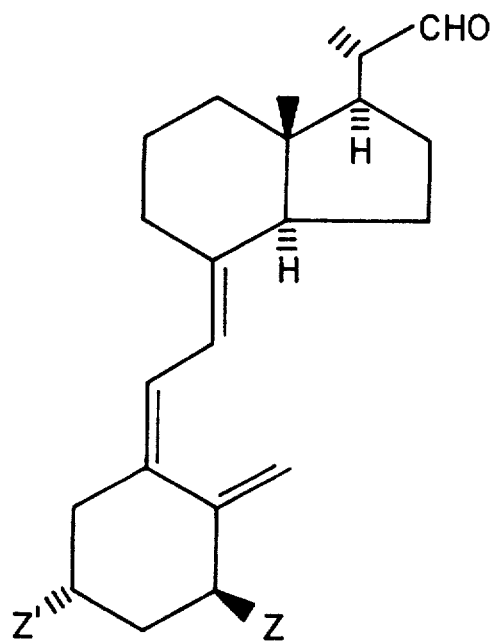

UNITED STATES PATENT AND TRADEMARK OFFICE
CERTIFICATE OF CORRECTION

PATENT NO. : 4,866,048

DATED : September 12, 1989

INVENTOR(S) : Calverley et al

It is certified that error appears in the above-identified patent and that said Letters Patent is hereby corrected as shown below:

Col. 11, Compound Numbers 26 and 27, "$-(CH_2-$" should be -- $-(CH_2)_2-$ --.

Col. 11, Compound Numbers 30 and 31, "$-(CH_2)_4-$" should be -- $-(CH_2)_5-$ --.

Col. 13, 1st line of Footnote (b) to Table 2,

"deparate" should be --separate--; and line 60, "$PhH-H_2$)" should be --$PhH-H_2O$--.

UNITED STATES PATENT AND TRADEMARK OFFICE
CERTIFICATE OF CORRECTION

PATENT NO. : 4,866,048
DATED : September 12, 1989
INVENTOR(S) : Calverley et al

It is certified that error appears in the above-identified patent and that said Letters Patent is hereby corrected as shown below:

Col. 15, line 11, "botton-half" should be --bottom-half--; and lines 33-49 should read:

--

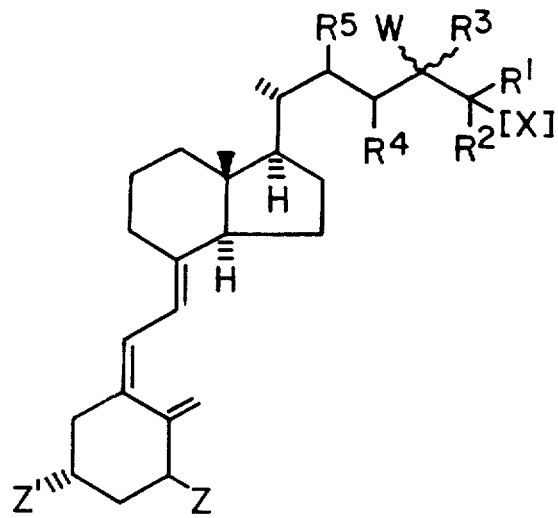

--

UNITED STATES PATENT AND TRADEMARK OFFICE
CERTIFICATE OF CORRECTION

PATENT NO. : 4,866,048

DATED : September 12, 1989

INVENTOR(S) : Calverley et al

It is certified that error appears in the above-identified patent and that said Letters Patent is hereby corrected as shown below:

Col. 18, line 63, "spits" should be --spots--.

Col. 19, line 64, "12 ethanol" should be --12 on elimination of $SO_2$) (1.12g) was suspended in 96% ethanol--.

Col. 21, line 57, "dulphox-" should be --sulphox- --; and line 59, "after" should be --After--.

Col. 22, line 60, "($Na_2S_2O$)" should be --($Na_2S_2O_4$)--.

Col. 24, line 8, "49.1" should be --4.91--.

Col. 25, line 37, "Purex" should be --Pyrex--.

Col. 30, line 51, "-20-3'-" should be -- -20-(3'- --; and line 57, "J 77" should be

UNITED STATES PATENT AND TRADEMARK OFFICE
CERTIFICATE OF CORRECTION

PATENT NO. : 4,866,048

DATED : September 12, 1989

INVENTOR(S) : Calverley et al

It is certified that error appears in the above-identified patent and that said Letters Patent is hereby corrected as shown below:

Col. 31, line 17, "hydroxypropyl-" should be --hydroxypropyl)- --.

Col. 32, line 64, "-20(3'-" should be -- -20-(3'- --.

Signed and Sealed this

Twenty-eighth Day of December, 1993

Attest:

BRUCE LEHMAN

Attesting Officer

Commissioner of Patents and Trademarks

UNITED STATES PATENT AND TRADEMARK OFFICE

CERTIFICATE EXTENDING PATENT TERM
UNDER 35 U.S.C. § 156

PATENT NO.       : 4,866,048

DATED            : September 12, 1989

INVENTOR(S)      : Martin J. Calverley et al.

PATENT OWNER     : Leo Pharmaceutical Products Ltd.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

473 DAYS from the original expiration date of the patent, September 12, 2006, subject to the requirements of 35 U.S.C. § 41, with all rights pertaining thereto as provided by 35 U.S.C. § 156(b).

I have caused the seal of the Patent and Trademark Office to be affixed this 25th day of April 1996.

Bruce A. Lehman
Assistant Secretary of Commerce and
   Commissioner of Patents and Trademarks